US010064834B2

(12) United States Patent
Ganapathy et al.

(10) Patent No.: US 10,064,834 B2
(45) Date of Patent: Sep. 4, 2018

(54) CARBIDOPA FOR THE TREATMENT OF CANCER

(71) Applicant: Texas Tech University System, Lubbock, TX (US)

(72) Inventors: Vadivel Ganapathy, Lubbock, TX (US); Yangzom D. Bhutia, Lubbock, TX (US); Babu Ellappan, Lubbock, TX (US); Sabarish Ramachandran, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 15/590,240

(22) Filed: May 9, 2017

(65) Prior Publication Data

US 2017/0319527 A1    Nov. 9, 2017

Related U.S. Application Data

(60) Provisional application No. 62/333,324, filed on May 9, 2016.

(51) Int. Cl.
*A61K 31/195* (2006.01)
*A61K 31/198* (2006.01)
*G01N 33/50* (2006.01)

(52) U.S. Cl.
CPC ....... *A61K 31/198* (2013.01); *G01N 33/5088* (2013.01); *G01N 2333/46* (2013.01); *G01N 2333/90241* (2013.01); *G01N 2333/912* (2013.01)

(58) Field of Classification Search
USPC ........................................................ 514/565
See application file for complete search history.

(56) References Cited

U.S. PATENT DOCUMENTS

| | | | |
|---|---|---|---|
| 7,799,782 B2 * | 9/2010 | Munson | C07D 231/56 514/234.5 |
| 7,863,336 B2 | 1/2011 | Yacoby-Zeevi et al. | |
| 8,324,280 B2 * | 12/2012 | Wafa | A61K 31/195 514/565 |
| 2004/0167216 A1 | 8/2004 | Xiang et al. | |

OTHER PUBLICATIONS

"1-Methyl-D-tryptophan in treating patients with metastatic or refractory solid tumors that cannot be removed by surgery." https://clinicaltrials.gov/ct2/show/NCT00567931, accessed Jun. 28, 2017.
"Guidance for Industry. Estimating the maximum safe starting dose in initial clinical trials for therapeutics in adult healthy volunteers." Food and Drug Administration, Center for Drug Evaluation and Research (CDER). (www.fda.gov/downloads/Drugs/Guidances/UCM078932.pdf).
Androutsopoulos, et al., "Cytochrome P450 CYP1A1: wider roles in cancer progression and prevention." BMC Cancer, Jun. 16, 2009, 9:187.
Bajaj, A. et al. "Parkinson's disease and cancer risk: a systematic review and meta-analysis". (2010) Cancer Causes Control 21, 597-707.
Braun, D., et al., "A two-step induction of indoleamine 2,3 dioxygenase (IDO) activity during dendritic-cell maturation." Blood, Oct. 1, 2005, 106(7):2375-2381.
Brod, et al., "Are high doses of carbidopa a concern? A randomized, clinical trial in Parkinson's disease." Mov Disord. May 2012, 27(6):750-753.
Coothankandaswamy, V. et al. "The amino acid transporter SLC6A14 is a novel and effective drug target for treatment of pancreatic cancer." (2016) Br J Pharmacol. 173, 3292-3306.
Feng, et al., "Role of aryl hydrocarbon receptor in cancer." Biochim Biophys Acta (2013) 1836:197-210.
Fung, et al., "Discovery and characterisation of hydrazines as inhibitors of the immune suppressive enzyme, indoleamine 2,3-dioxygenase 1 (IDO1)." Bioorg Med Chem. (2013) 21:7595-7603.
Hall, et al., "Activation of the aryl hydrocarbon receptor inhibits invasive and metastatic features of human breast cancer cells and promotes breast cancer cell differentiation." Mol Endocrinol. Feb. 2010, 24(2):359-369.
Hanieh, et al., "Novel aryl hydrocarbon receptor agonist suppresses migration and invasion of breast cancer cells." PLoS ONE Dec. 1, 2016, 11(12):e0167650.
Hwu, et al., "Indoleamine 2,3-dioxygenase production by human dendritic cells results in the inhibition of T cell proliferation." J Immunol. (2000) 164:3596-3599.
Inzelberg, et al., "The particular relationship between Parkinson's disease and malignancy: a focus on skin cancers." J Neural Transm. (2009) 116:1503-1507.
Jin, et al., "Microbiome-derived tryptophan metabolites and their aryl hydrocarbon receptor-dependent agonist and antagonist activities." Mol Pharmacol. May 2014, 85:777-88.
Koliopanos, et al., "Increased arylhydrocarbon receptor expression offers a potential therapeutic target for pancreatic cancer." Oncogene (2002) 21:6059-6070.
LeWitt, P.A. "Levodopa therapy for Parkinson's disease: Pharmacokinetics and pharmacodynamics." (2015) Mov Disord. 30, 64-72.

(Continued)

*Primary Examiner* — Rei Tsang Shiao
(74) *Attorney, Agent, or Firm* — Edwin S. Flores; Daniel J. Chalker; Chalker Flores, LLP

(57) ABSTRACT

The present invention includes a method of inhibiting or reducing mTOR signaling or inhibition of indoleamine dioxygenase-1 (IDO1) in a subject with a proliferative disease, which comprises administering to the subject having or suspected to have the proliferative disease, a therapeutically or prophylactically effective amount of the compound of Formula I:

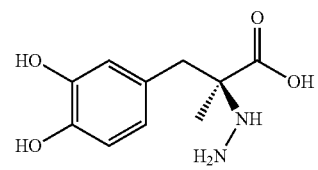

or a pharmaceutically acceptable salt or solvate thereof.

34 Claims, 9 Drawing Sheets
Specification includes a Sequence Listing.

(56) References Cited

OTHER PUBLICATIONS

Mellor, A.L. et al. "Creating immune privilege: active local suppression that benefits friends, but protects foes." Jan. 2008 Nat Rev Immunol. 8, 74-80.

Muller, A.J. et al. "Targeting the mechanisms of tumoral immune tolerance with small-molecule inhibitors." Aug. 2006, Nat Rev Cancer 6, 613-625.

Munn, D.H. "Indoleamine 2,3-dioxygenase, tumor-induced tolerance and counter-regulation." (2006) Curr Opin Immunol. 18, 220-225.

Munn, D.H. et al. "Potential regulatory function of human dendritic cells expressing indoleamine 2,3-dioxygenase." Sep. 13, 2002, Science 297, 1867-1870.

Munn, et al., "Expression of indoleamine 2,3-dioxygenase by plasmacytoid dendritic cells in tumor-draining lymph nodes." J Clin Invest. Jul. 2004, 114(2):280-290.

Munn, et al., "Indoleamine 2,3-dioxygenase and tumor-induced tolerance." J Clin Invest. May 2007, 117(5):1147-1154.

Murray, et al., "Aryl hydrocarbon receptor ligands in cancer: friend or foe." Nat Rev Cancer Dec. 2014, 14(12):801-814.

Nagatsua, T. et al. "L-Dopa therapy for Parkinson's disease: past, present, and future." Parkinsonism Relat Disord. 15(2009) (Suppl 1), S3-S8.

Nikolaou, et al., "Emerging trends in the epidemiology of melanoma." Br J Dermatol. (2014) 170:11-19.

Opitz, et al., "An endogenous tumour-promoting ligand of the human aryl hydrocarbon receptor." Nature Oct. 13, 2011, 478:197-203.

Reagan-Shaw, et al., "Dose translation from animal to human studies revisited." FASEB J. Mar. 2007, 22(3):659-661.

Siple, et al., "Levodopa therapy and the risk of malignant melanoma." Ann Pharmacother. Mar. 2000, 34:381-385.

Sun, L.M. et al. Analysis of Parkinson's disease and subsequent cancer risk in Taiwan: a nationwide population-based cohort study. (2011) Neuroepidemiology 37, 114-119.

Taylor, et al., "Relationship between interferon-gamma, indoleamine 2,3-dioxygenase, and tryptophan catabolism." FASEB J. Aug. 1991, 5:2516-2522.

Vacchelli, et al., "Trial watch: IDO inhibitors in cancer therapy." Oncoimmunology Nov. 1, 2014, 3:e957994.

Vermeij, et al., "Parkinson's disease, levodopa-use and the risk of melanoma." Parkinsonism Relat Disord. (2009) 15:551-553.

Zanetti, R. et al. "Melanoma, Parkinson's disease and levodopa: causal or spurious link? A review of the literature." (2006) Melanoma Res. 16, 201-206.

\* cited by examiner

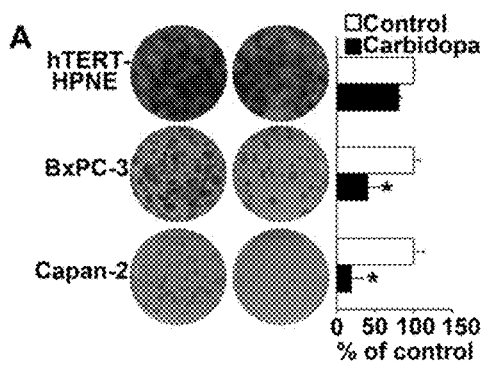
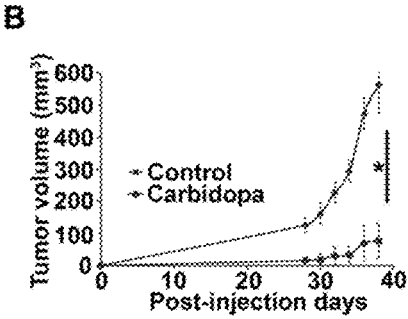
FIG. 9A  FIG. 9B
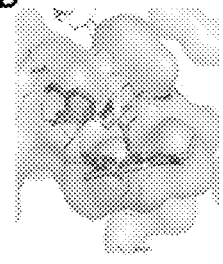
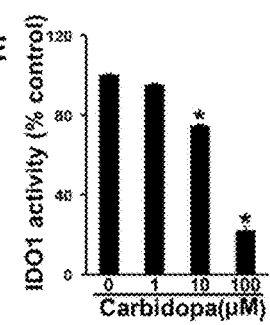
FIG. 9C  FIG. 9D  FIG. 9E
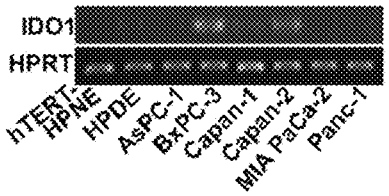
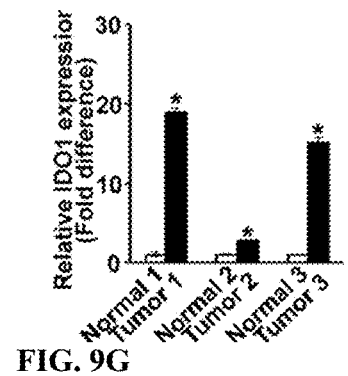
FIG. 9F  FIG. 9G
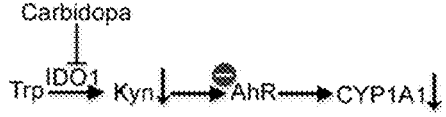
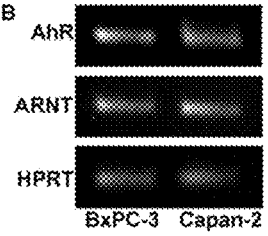
FIG. 10A  FIG. 10B

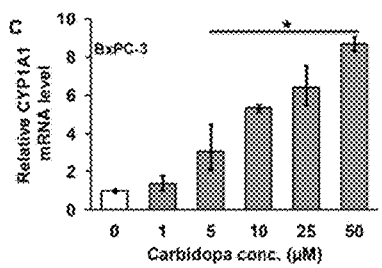
FIG. 10C
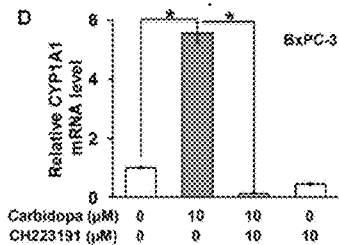
FIG. 10D
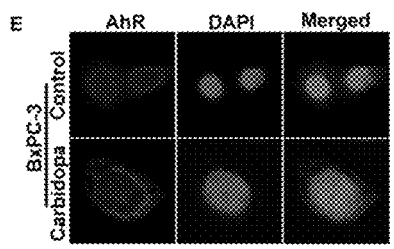
FIG. 10E
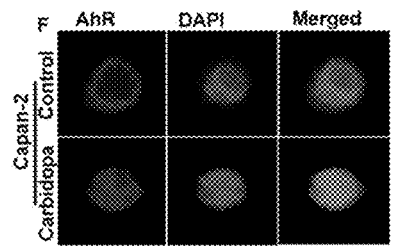
FIG. 10F
Figure 2
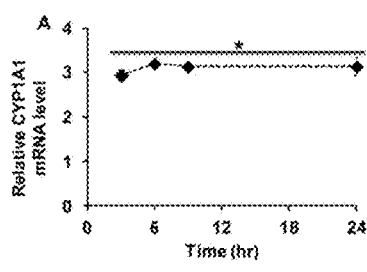
FIG. 11A
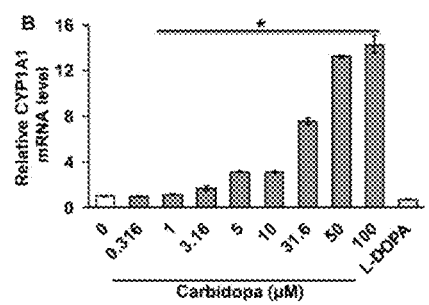
FIG. 11B
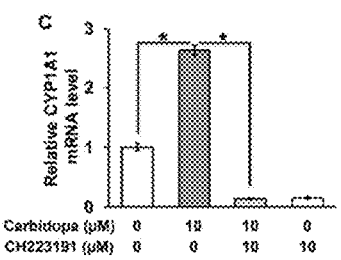
FIG. 11C
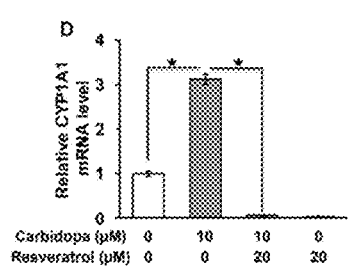
FIG. 11D
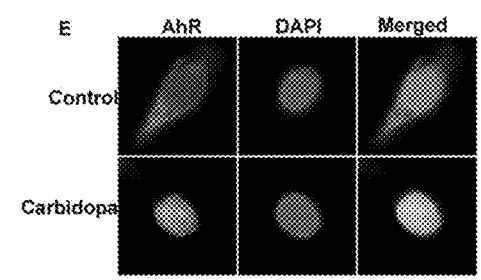
FIG. 11E
Figure 3

SEQUENCE LISTING

```
<160> NUMBER OF SEQ ID NOS: 10

<210> SEQ ID NO 1
<211> LENGTH: 21
<212> TYPE: DNA
<213> ORGANISM: Homo sapiens

<400> SEQUENCE: 1
caggcagatg tttagcaatg a                                               21

<210> SEQ ID NO 2
<211> LENGTH: 20
<212> TYPE: DNA
<213> ORGANISM: Homo sapiens

<400> SEQUENCE: 2
gatgaagaag tgggctttgc                                                 20

<210> SEQ ID NO 3
<211> LENGTH: 20
<212> TYPE: DNA
<213> ORGANISM: Homo sapiens

<400> SEQUENCE: 3
tcaaatcctt ccaagcggca                                                 20

<210> SEQ ID NO 4
<211> LENGTH: 20
<212> TYPE: DNA
<213> ORGANISM: Homo sapiens

<400> SEQUENCE: 4
acagttatcc tggcctccgt                                                 20
```

```
<210> SEQ ID NO 5
<211> LENGTH: 23
<212> TYPE: DNA
<213> ORGANISM: Homo sapiens

<400> SEQUENCE: 5
ccggcagaga atttcaggaa tag                                              23

<210> SEQ ID NO 6
<211> LENGTH: 20
<212> TYPE: DNA
<213> ORGANISM: Homo sapiens

<400> SEQUENCE: 6
gaaagctgcc cacaccaaac                                                  20

<210> SEQ ID NO 7
<211> LENGTH: 24
<212> TYPE: DNA
<213> ORGANISM: Homo sapiens

<400> SEQUENCE: 7
gcgtcgtgat tagcgatgat gaac                                             24

<210> SEQ ID NO 8
<211> LENGTH: 24
<212> TYPE: DNA
<213> ORGANISM: Homo sapiens

<400> SEQUENCE: 8
cctcccatct ccttcatgac atct                                             24

<210> SEQ ID NO 9
<211> LENGTH: 20
<212> TYPE: DNA
<213> ORGANISM: Homo sapiens

<400> SEQUENCE: 9 caagggggcgt tgtgtctttg                                                 20

<210> SEQ ID NO 10
<211> LENGTH: 20
<212> TYPE: DNA
<213> ORGANISM: Homo sapiens

<400> SEQUENCE: 10
gtcgatagca ccatcagggg                                                  20
```

CARBIDOPA FOR THE TREATMENT OF CANCER

CROSS-REFERENCE TO RELATED APPLICATIONS

This application claims priority to U.S. Provisional Application Ser. No. 62/333,324, filed May 9, 2016, the entire contents of which are incorporated herein by reference.

TECHNICAL FIELD OF THE INVENTION

The present invention relates in general to the field of cancer treatment, and more particularly, to the use of Carbidopa for the treatment of cancer.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with treatments using Carbidopa.

U.S. Pat. No. 7,863,336, issued to Yacoby-Zeevi, et al., entitled, "Continuous administration of DOPA decarboxylase inhibitors and compositions for same," is directed to compositions that include for example the arginine salts of Carbidopa, and methods for treating neurological or movement diseases or disorders such as restless leg syndrome, Parkinson's disease, secondary parkinsonism, Huntington's disease, Parkinson's like syndrome, PSP, MSA, ALS, Shy-Drager syndrome and conditions resulting from brain injury including carbon monoxide or manganese intoxication, using substantially continuous administration of Carbidopa or salt thereof together with administration of levodopa.

United States Patent Application Publication No. 2004/0167216, filed by Xiang, Jia-Ning, et al., is entitled "Carbidopa prodrugs and derivatives, and compositions and uses thereof." These applicants teach prodrugs of Carbidopa, derivatives of Carbidopa prodrugs, methods of making prodrugs of Carbidopa and derivatives thereof, methods of using prodrugs of Carbidopa and derivatives thereof, and compositions of prodrugs of Carbidopa and derivatives thereof are disclosed.

SUMMARY OF THE INVENTION

The present invention includes a method of inhibiting or reducing mTOR signaling or inhibition of indoleamine dioxygenase-1 (IDO1) in a subject with a proliferative disease which comprises administering to the subject having or suspected to have the proliferative disease, a therapeutically or prophylactically effective amount of the compound of Formula I:

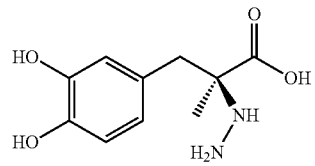

or a pharmaceutically acceptable salt or solvate thereof. In one aspect, the proliferative disease is selected from at least one of a leukemia, myeloma, myeloproliferative disease, myelodysplastic syndrome, idiopathic hypereosinophilic syndrome (HES), bladder cancer, breast cancer, Estrogen Receptor (ER)-negative or mutant BRCA-driven breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the therapeutically or prophylactically effective amounts of the compound are from about 15 to 500, 25 to 450, 50 to 400, 70 to 100, 100 to 350, 150 to 300, 200 to 250, 15, 25, 50, 75, 100, 150, 200, 250, 300, 400, 450, 500 or 600 mg per day. In another aspect, the compound is administered at least one of continuously, intermittently, systemically, or locally. In another aspect, the IDO1 is defined further as a human IDO1. In another aspect, the compound is administered orally, intravenously, or intraperitoneally. In another aspect, the Carbidopa is at least one of Carbidopa Besylate, Carbidopa Phosphate, Carbidopa Lactate, Carbidopa Hydrochloride, Carbidopa Citrate, Carbidopa Acetate, Carbidopa Toluene-sulphonate, Carbidopa Succinate, or Carbidopa Besylate. In another aspect, the mTOR is a human mTOR. In another aspect, the therapeutically or prophylactically effective amount of compound is administered daily for as long as the subject is in need of treatment for the proliferative disease. In another aspect, the compound is provided at least one of sequentially or concomitantly, with another pharmaceutical agent in a newly diagnosed proliferative disease subject, to maintain remission of an existing subject, or a relapsed/refractory proliferative disease subject. In another aspect, the compound is provided as a single agent or in combination with another pharmaceutical agent in a newly diagnosed proliferative disease subject, to maintain remission, or a relapsed/refractory proliferative disease subject. In another aspect, the compound is provided as a single agent or in combination with another pharmaceutical agent in a newly diagnosed proliferative disease pediatric subject, to maintain remission, or a relapsed/refractory proliferative disease pediatric. In another aspect, the compound is provided in an amount sufficient to inhibit or reduce mTOR signaling or inhibit IDO1.

The present invention also includes a method for treating a subject with a proliferative disease comprising: administering to the subject in need of such treatment, a therapeutically effective amount of Carbidopa or a salt thereof, wherein the cell proliferative disorder is characterized by the need to inhibit or reduce mTOR signaling or inhibit IDO1, wherein the proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, or hematologic malignancy. In another aspect, the compound is administered orally, intravenously, or intraperitoneally. In another aspect, the Carbidopa is at least one of Carbidopa Besylate, Carbidopa Phosphate, Carbidopa Lactate, Carbidopa Hydrochloride, Carbidopa Citrate, Carbidopa Acetate, Carbidopa Touluenesulphonate, Carbidopa Succinate or Carbidopa Besylate. In another aspect, the Carbidopa is provided at least one of sequentially or concomitantly, with chemotherapy, radiotherapy, or surgery in a newly diagnosed proliferative disease, to maintain remission, or a relapsed/refractory proliferative disease. In another aspect, the Carbidopa is provided as a single agent or in combination with chemotherapy, radiotherapy or surgery for treatment of pediatric subject with the proliferative disease. In another aspect, the Carbidopa is provided as a single agent to at least one of post standard induction therapy, or high dose induction therapy, in newly diagnosed proliferative disease. In another aspect, the Carbidopa is provided as a single agent in treatment of subjects with the proliferative disease that is either refractory to, or has relapsed after, standard or high dose chemotherapy, radiotherapy or surgery. In another aspect, the subject is refractory to a prior anti-neoplastic therapy. In another aspect, the method further comprises the step of identifying a subject in need of treatment for a proliferative disease prior to treatment.

The present invention includes a method for treating a subject with breast or pancreatic cancer comprising: obtaining a sample from the subject suspected of having breast or pancreatic cancer; determining from the subject sample that the subject has a need of inhibiting or reducing mTOR signaling or inhibition of indoleamine dioxygenase-1 (IDO1); and administering to the subject in need of such treatment a therapeutically effective amount of Carbidopa or a salt thereof, wherein the breast or pancreatic cancer is characterized by the need to inhibit or reduce mTOR signaling or inhibit IDO1.

The present invention also includes a method for specifically inhibiting or reducing mTOR signaling or inhibition of indoleamine dioxygenase-1 (IDO1) comprising: determining if a subject has a proliferative disease; obtaining a subject sample to determine a need to inhibit or reduce mTOR signaling or inhibit IDO1; and administering to a mammal in need of such treatment a therapeutically effective amount of Carbidopa or a salt thereof sufficient inhibit or reduce mTOR signaling or inhibit IDO1 in the mammal. In another aspect, the proliferative disease is selected from at least one of a leukemia, myeloma, myeloproliferative disease, myelodysplastic syndrome, idiopathic hypereosinophilic syndrome (HES), bladder cancer, breast cancer, Estrogen Receptor (ER)-negative or mutant BRCA-driven breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the therapeutically and prophylactically effective amounts of Carbidopa or a salt thereof are from about 15 to 500 mg per day. In another aspect, the Carbidopa or a salt thereof is administered at least one of continuously, intermittently, systemically, or locally. In another aspect, the mTOR is a human mTOR. In another aspect, the compound is administered orally, intravenously, or intraperitoneally. In another aspect, the Carbidopa is at least one of Carbidopa Besylate, Carbidopa Phosphate, Carbidopa Lactate, Carbidopa Hydrochloride, Carbidopa Citrate, Carbidopa Acetate, Carbidopa Touluenesulphonate and Carbidopa Succinate Carbidopa Besylate. In another aspect, the IDO1 is a human IDO1. In another aspect, the therapeutically or prophylactically effective amount of the compound is administered daily for as long as the subject is in need of treatment for the proliferative disease. In another aspect, the subject is provided treatment, and the method further comprises the steps of: obtaining one or more subject samples to determine the effect of the treatment, and continuing treatment until the proliferative disease is reduced or eliminated. In another aspect, the compound is provided at least one of sequentially or concomitantly, with another pharmaceutical agent in a newly diagnosed proliferative disease subject, to maintain remission, or a relapsed/refractory proliferative disease subject. In another aspect, the compound is provided as a single agent or in combination with another pharmaceutical agent in a newly diagnosed proliferative disease subject, to maintain remission, or a relapsed/refractory proliferative disease subject. In another aspect, the compound is provided as a single agent or in combination with another pharmaceutical agent in a newly diagnosed proliferative disease pediatric subject, to maintain remission, or a relapsed/refractory proliferative disease pediatric subject.

The present invention further includes a method of determining the effectiveness of Carbidopa or an active derivative thereof, the method comprising: (a) measuring the serum or plasma based levels of mTOR signaling or of indoleamine dioxygenase-1 (IDO1); (b) administering the candidate drug to a first subset of the patients, and a placebo to a second subset of the patients; (c) determining the activity of mTOR signaling or indoleamine dioxygenase-1 (IDO1) in the first and second subset of patients; (d) determining if the Carbidopa or the active derivative thereof reduce or inhibit mTOR signaling or indoleamine dioxygenase-1 activity; (e) repeating step (a) after the administration of the candidate drug or the placebo; and (f) determining if the candidate drug modifies the activity of mTOR signaling or IDO1 over the course of the treatment.

BRIEF DESCRIPTION OF THE DRAWINGS

For a more complete understanding of the features and advantages of the present invention, reference is now made to the detailed description of the invention along with the accompanying figures and in which.

Breast cancer occurs in different subtypes: estrogen receptor-positive, estrogen receptor-negative, and BRCA1-mutant.

Figure 6:
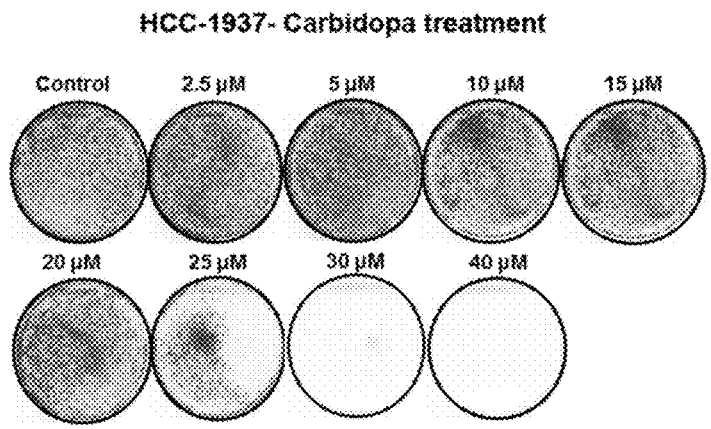

FIG. 6 shows the effect of Carbidopa on the growth of BRCA-1 mutant breast cancer cells in vitro. Breast cancer occurs in different subtypes: estrogen receptor-positive, estrogen receptor-negative, and BRCA1-mutant. Mutations in BRCA-1 represent a small percentage of breast cancers in women but the disease is inheritable.

Figure 7:
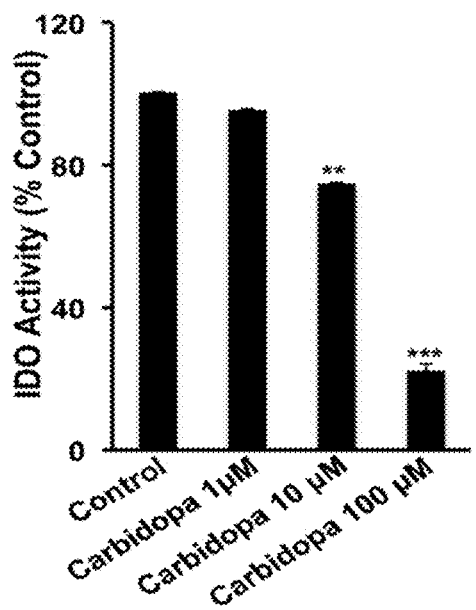

FIG. 7 is a graph that shows the effect of Carbidopa on the enzyme activity of recombinant human indoleamine dioxygenase-1 (IDO1). IDO-1 is an immunosuppressive enzyme that is induced in tumor cells and in immune cells present in tumor-draining lymph nodes.

Figure 8:
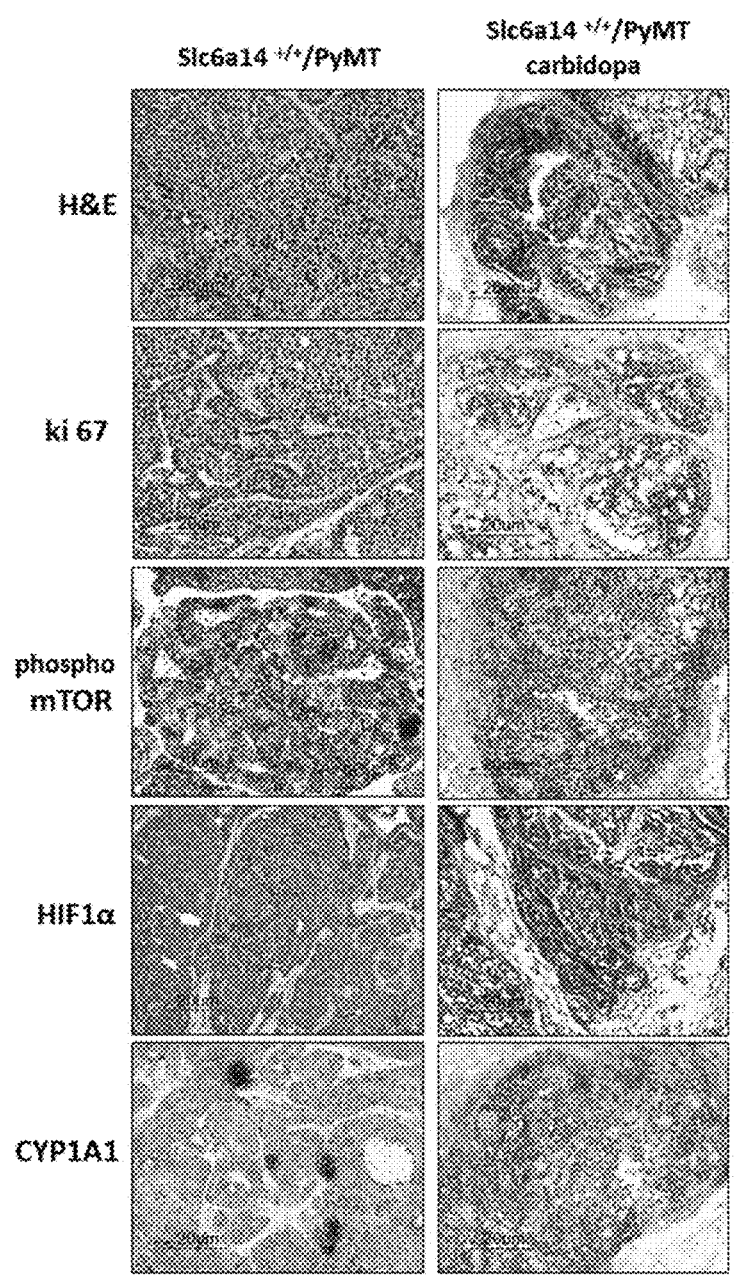

FIG. 8 is an immunohistochemical analysis of Ki-67, p-mTOR, HIF1α and Cyp1a1 protein expression in MMTV-PyMT-Tg mice treated with and without Carbidopa. Ki-67 staining shows a significant difference in cell proliferation with a marked reduction in proliferation in Carbidopa-treated mice.

FIGS. 9A to 9G. Inhibition of pancreatic cancer cell proliferation by Carbidopa and possible relevance of IDO1 inhibition to the process. (FIG. 9A) Clonogenic assay in human pancreatic normal (hTERT-HPNE) and cancer cell lines (BxPC-3 and Capan-2) cultured in the presence and absence of Carbidopa (10 μM) for two weeks and stained with KaryoMax Giemsa stain. Data are given as means±S.D. *, P<0.05. (FIG. 9B) Subcutaneous xenograft of BxPC-3 cells in athymic nude mice demonstrating difference in tumor volume between control and the Carbidopa treated group. *, P<0.05 at all time points. (FIG. 9C) Docking simulation of phenylhydrazine to the active site of IDO1, suggesting its potential to bind to heme at the active of the enzyme. (FIG. 9D) Docking simulation of Carbidopa to IDO1 suggesting its potential to bind heme at the active site of the enzyme. (FIG. 9E) IDO1 enzymatic activity assay using recombinant human enzyme in the presence and absence of Carbidopa showing its ability to inhibit the enzyme. Data are given as means±S.D. *, P<0.05. (FIG. 9F) RT-PCR for the expression of IDO1 in pancreatic normal (hTERT-HPNE and HPDE) and cancer cell lines (AsPC-1, BxPC-3, Capan-1, Capan-2, MIA PaCa-2, and Panc-1). HPRT was taken as an endogenous control. (FIG. 9G) Real-time PCR showing the relative expression of IDO1 in pancreatic normal tissue and its matched adjacent tumor tissues. Data are given as means±SEM. *, P<0.05.

FIGS. 10A to 10F. Carbidopa induces CYP1A1 expression in an AhR-dependent manner in pancreatic cancer cells. (FIG. 10A) Rationale for using AhR activation and its downstream target gene CYP1A1 expression as a readout for the inhibition of IDO1 by Carbidopa. (FIG. 10B) RT-PCR demonstrating the expression of AhR and ARNT in pancreatic cancer cell lines (BxPC-3 and Capan-2). HPRT was taken as an endogenous control. (FIG. 10C) Real-time PCR demonstrating the increase in CYP1A1 expression in BxPC-3 cells following 6-h treatment with varying concentrations of Carbidopa (1, 5, 10, 25, and 50 μM). Columns, relative to control of triplicate. Error bars indicate 95% confidence interval estimates of the mean expressions (n=3). *, P<0.05 compared to untreated control. (FIG. 10D) Real-time PCR showing the relative CYP1A1 expression in BxPC-3 cells following 6-h treatment with Carbidopa (10 μM) in the presence or absence of the AhR antagonist CH223191 (10 μM). Columns, relative to control of triplicate. Error bars indicate 95% confidence interval estimates of the mean expressions (n=3). *, P<0.05. (FIG. 10E, FIG. 10F) Immunofluorescence detection of AhR (green) in control and Carbidopa-treated (25 μM for 6 h) BxPC-3 and Capan-2 cells. Nuclei stained with DAPI are blue. Magnification, 100×.

FIGS. 11A to 11E. Carbidopa induces CYP1A1 expression in an AhR-dependent manner in HepG2, a human liver cancer cell line (FIG. 1A) Relative CYP1A1 mRNA expression following treatment of HepG2 cells with 10 μM Carbidopa for various time intervals (6, 12, 18, and 24 h). Points, relative to control of triplicate. Error bars indicate 95% confidence interval estimates of the mean expressions (n=3). *, P<0.05 compared to untreated control, which was taken as 1. (FIG. 11B) Relative CYP1A1 mRNA expression in HepG2 cells cultured in the absence and presence of varying concentrations of Carbidopa (0.316, 1, 3.16, 5, 10, 31.6, 50, and 100 μM) and L-DOPA (100 μM) for 6 h. Columns, relative to control of triplicate. Error bars indicate 95% confidence interval estimates of the mean expressions (n=3). *, P<0.05 compared to untreated control. (FIG. 11C, FIG. 11D) Relative CYP1A1 mRNA expression in HepG2 cells treated with Carbidopa (10 μM) in the presence or absence of two different AhR antagonists: CH223191 (10 μM) and resveratrol (20 μM) for 6 h. Columns, relative to control of triplicate. Error bars indicate 95% confidence interval estimates of the mean expressions (n=3). *, P<0.05. (FIG. 11E) Immunofluorescence detection of AhR (green) in control and Carbidopa-treated (25 μM for 6 h) HepG2 cells. Nuclei stained with DAPI are blue. Magnification, 100×.

Figure 12A:
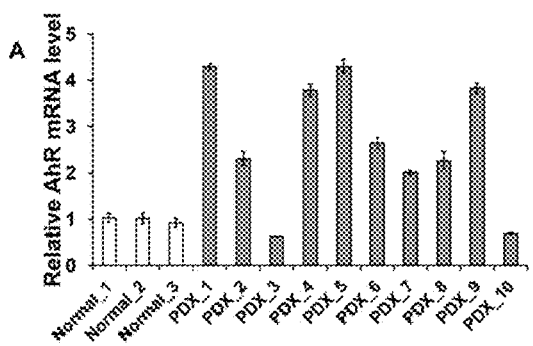
Figure 12B:
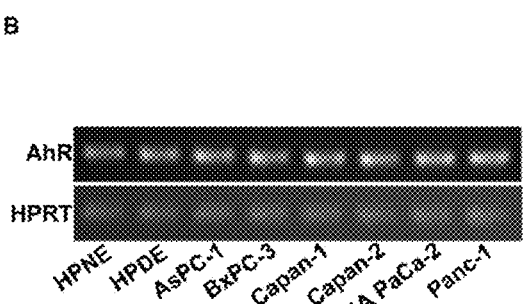
Figure 12C:
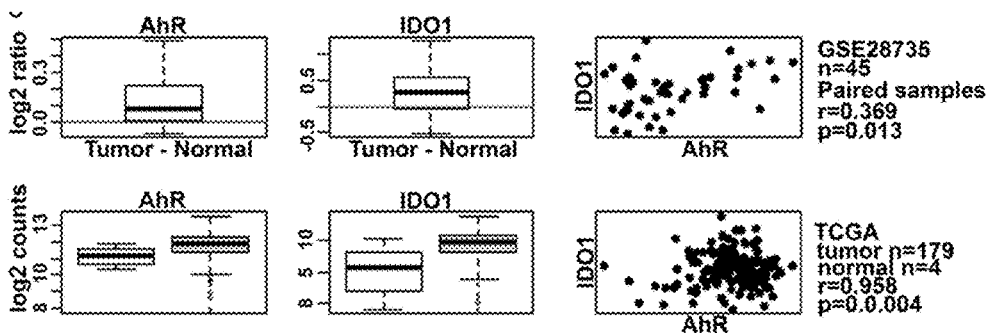

FIGS. 12A to 12C. Increased expression of AhR and IDO1 in pancreatic cancer and possible direct relationship between the expression levels of the two genes. (FIG. 12A) Real-time PCR showing relative AhR expression in pancreatic normal tissues vs patient-derived xenografts (PDXs) of pancreatic cancer. Columns, relative to normal of triplicate. Error bars indicate 95% confidence interval estimates of the mean expressions (n=3). (FIG. 12B) RT-PCR showing the expression of AhR in pancreatic normal (hTERT-HPNE and HPDE) and cancer cell lines (AsPC-1, BxPC-3, Capan-1, Capan-2, MIA PaCa-2, and Panc-1). HPRT was taken as an endogenous control. (FIG. 12C) Box plots for the expression of AhR and IDO1 in pancreatic tumor tissues compared to pancreatic normal tissue, as assessed from the publically available microarray datasets. The horizontal line within each box represents the median value. The box edges represent the lower ($25^{th}$) and upper ($75^{th}$) quartile.

Figure 13:
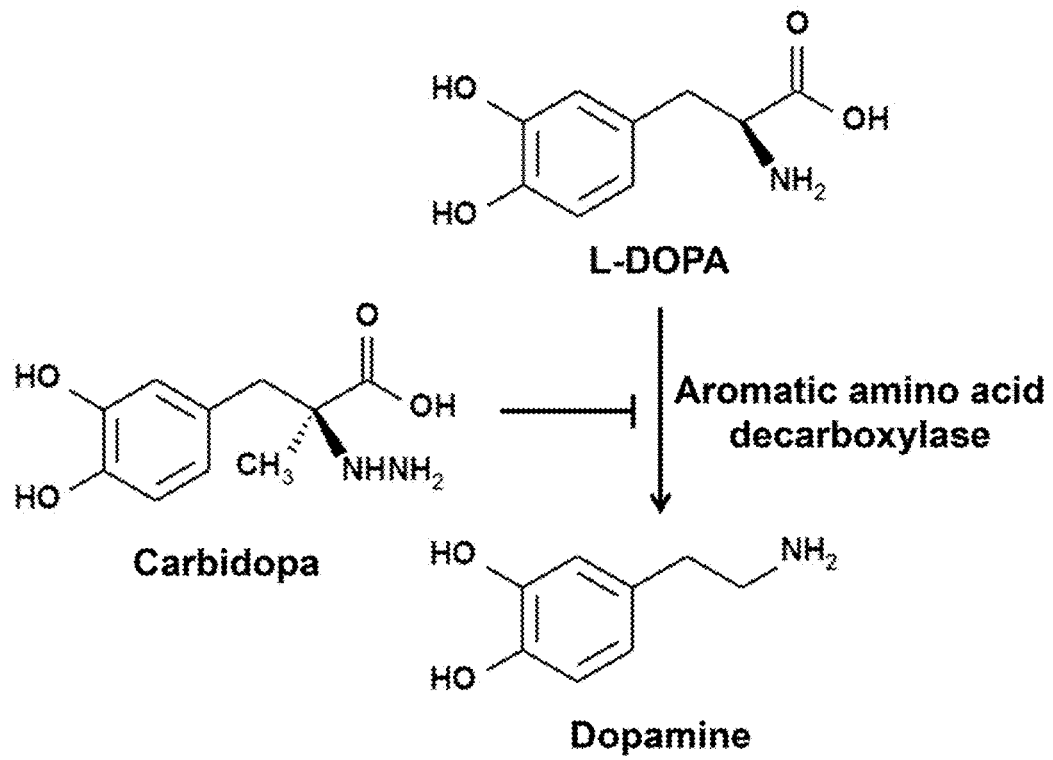

FIG. 13. Structure and the known mechanism of Carbidopa as an anti-Parkinsonian drug. Carbidopa prevents the conversion of L-DOPA into dopamine in the periphery by inhibiting the enzyme aromatic amino acid decarboxylase.

Figure 14:
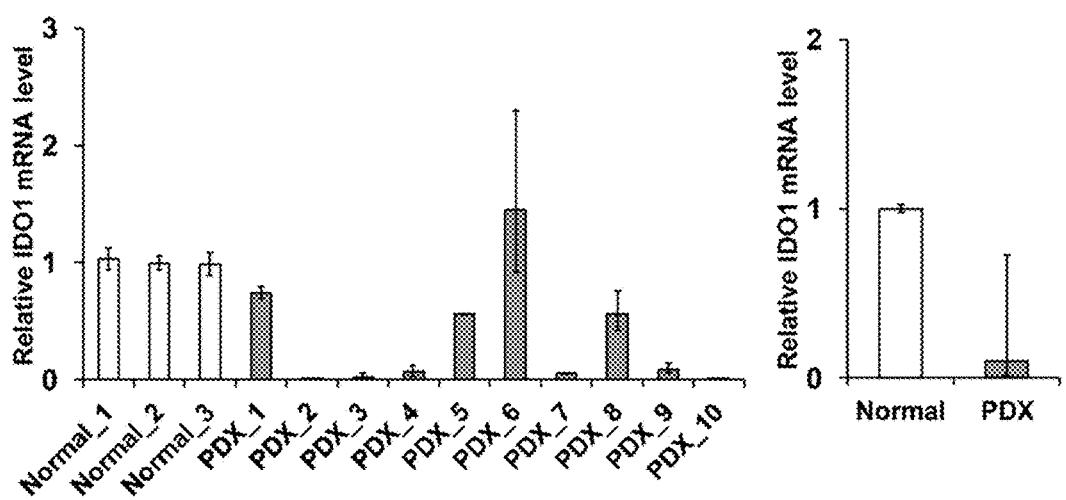

FIG. 14. IDO1 expression in human normal pancreatic tissue and in patient-derived xenografts (PDXs) of pancreatic cancer. Real-time PCR showing relative IDO1 expression in PDXs compared to the normal pancreatic tissues. Columns, relative to normal of triplicate. Error bars indicate 95% confidence interval estimates of the mean expressions (n=3).

FIGS. 15A to 15D. Activation of AhR by Carbidopa in the human pancreatic cancer cell lines Capan-2 and BxPC-3. (FIG. 15A) Relative CYP1A1 mRNA expression in Capan-2 cells cultured in the absence and presence of varying concentrations of Carbidopa (1, 5, 10, 25, and 50 μM) for 6 h. (FIG. 15B, FIG. 15C) Real-time PCR showing inhibition of Carbidopa-induced CYP1A1 expression following treatment with AhR antagonists CH223191 and resveratrol in Capan-2 cells. (FIG. 15D) Real-time PCR showing inhibition of Carbidopa-induced CYP1A1 expression following treatment with resveratrol in BxPC-3 cells. Columns, relative to normal of triplicate. Error bars indicate 95% confidence interval estimates of the mean expressions (n=3). *, P<0.05 compared to untreated control.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined here in have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Abbreviations: L-DOPA, L-3,4-dihydroxyphenylalanine; IDO1, indoleamine 2,3-dioxygenase; AhR, aryl hydrocarbon receptor; CYP1A1, cytochrome P450 family 1 subfamily A member 1: FBS, fetal bovine serum; DMEM, Dulbecco's Modified Eagles Medium; HPRT1, hypoxanthine phosphoribosyltransferase; DAPI, 4',6-diamidino-2-phenyllindole, dihydrochloride; PDX, patient-derived xenograft; DRE, dioxin response element.

Carbidopa is an FDA-approved drug used in the treatment of Parkinson's disease in conjunction with Levo-Dopa. Carbidopa ((2S)-3-(3,4-dihydroxyphenyl)-2-hydrazino-2-methylpropanoic acid) itself has no effects without the use of Levo-dopa in neurological conditions, and these two medications are prescribed together for treatment of Parkinson's disease.

A used herein, a "pharmaceutically effective amount" or "therapeutically effective amount" refers to that amount of an agent effective to produce the intended effect of reducing, preventing and/or treating cancer. The cancer may be caused by gene deregulation or deregulation of metabolic activities. Such factors include upregulation of mTOR driven cell cycle proliferation or the upregulation of indoleamine dioxygenase-1 (IDO1) enabling the cancer cells to evade the immune system.

A pharmaceutical composition refers to a composition suitable for pharmaceutical use in an animal or animal cell line. The animal may be a mammal, such as a human. A pharmaceutical composition of the invention includes a pharmaceutically effective amount of a Carbidopa, Carbidopa derivative, or salt thereof, in a pharmaceutically acceptable carrier.

Techniques and compositions for making useful dosage forms using the present invention are described in one or more of the following references: Anderson, Philip O.; Knoben, James E.; Troutman, William G, eds., HANDBOOK OF CLINICAL DRUG DATA, Tenth Edition, McGraw-Hill, 2002; Pratt and Taylor, eds., PRINCIPLES OF DRUG ACTION, Third Edition, Churchill Livingston, N.Y., 1990; Katzung, ed., BASIC AND CLINICAL PHARMACOLOGY, Ninth Edition, McGraw Hill, 2007; Goodman and Gilman, eds., THE PHARMACOLOGICAL BASIS OF THERAPEUTICS, Tenth Edition, McGraw Hill, 2001; REMINGTON'S PHARMACEUTICAL SCIENCES, 20th Ed., Lippincott Williams & Wilkins., 2000; Martindale, THE EXTRA PHARMACOPOEIA, Thirty-Second Edition (The Pharmaceutical Press, London, 1999); as well as newer editions of each of the above, all of which are incorporated by reference, and the like, relevant portions incorporated herein by reference.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that (those) named purpose(s) or function(s).

Most cancers are difficult to treat, and almost all currently used anticancer drugs have limited efficacy and significant side effects. Identification of new drugs in cancer therapy is sorely needed. Carbidopa fulfills this dire need. Carbidopa is orally bioavailable; therefore, it can be used as an orally active drug for the treatment of cancers.

Example 1

The present inventors demonstrate that Carbidopa alone can be used as an effective anticancer drug for the treatment of pancreatic cancer and breast cancer in mouse models. This drug has been shown to inhibit mTOR signaling pathway and also indoleamine dioxygenase-1 (IDO1), an immunosuppressive enzyme induced in tumor cells, thus allowing Carbidopa to treat cancers by multiple mechanisms. The present inventors also demonstrate that Carbidopa alone can inhibit the growth and proliferation of human breast cancer cell lines that represent various subtypes of breast cancer known in humans (estrogen receptor-positive, triple-negative, and BRCA1-mutant). Additionally, even though this drug works as an anticancer drug when administered by itself, it can be used easily in combination with other routinely used chemotherapeutic agents to boost the anticancer efficacy.

These studies demonstrate that Carbidopa is effective in the treatment of cancer, including pancreatic and breast cancer, which are some of the most difficult to treat cancers, in a mouse xenograft model. It is also effective in the treatment of spontaneous mouse models of breast cancer and colon cancer. It is also effective in killing a wide variety of breast cancer cell lines in vivo and in vitro. A possible mechanism of action, but in no way a limitation of the present invention, of Carbidopa as an anticancer drug in vivo may include: (a) inhibition of amino acid entry into cancer cells, (b) inhibition of the immunosuppressive enzyme indoleamine 2,3-dioxygenase-1, thus increasing the ability of the immune system to recognize cancer cells as foreign cells and kill them, and/or (c) inhibition of the generation of the stress hormones norepinephrine and epinephrine that promote cancer growth and progression. Thus, Carbidopa might work via multiple targets resulting in amino acid starvation in cancer cells, increasing the potency of anticancer immunity, and reducing stress hormones. As some of these mechanisms are likely to be common for a wide variety of cancers, the use of Carbidopa of the present invention has a broader therapeutic scope as an anticancer drug.

Figure 1:
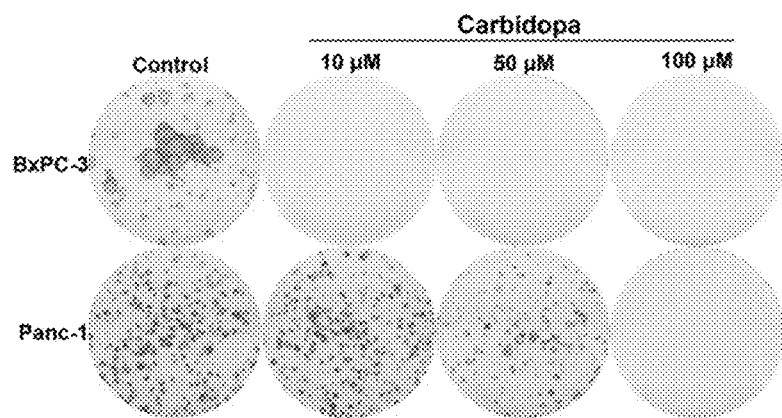
FIG. 1 shows the effect of Carbidopa (dose response) on the growth of human pancreatic cancer cell lines BxPC-3 and Panc-1. Colony formation assay was used to assess the effect. The growth of BxPC-3 cells was almost completely abolished at 10 µM Carbidopa.

FIG. 1 shows the effect of Carbidopa (dose response) on the growth of human pancreatic cancer cell lines BxPC-3 and Panc-1. Colony formation assay was used to assess the effect. The growth of BxPC-3 cells was almost completely abolished at 10 µM Carbidopa. With regard to Panc-1 cells, 50% inhibition of growth was observed at Carbidopa concentrations <50 µM.

Figure 2A:
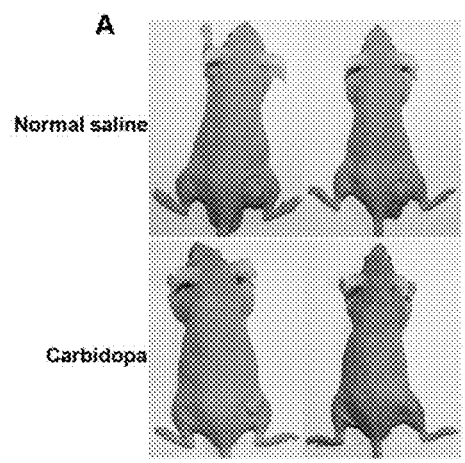
FIGS. 2A and 2B show the in vivo effect of Carbidopa on the growth of BxPC-3 cells in mouse xenografts (2A: mice and 2B: a graph showing the tumor volume).
Figure 2B:
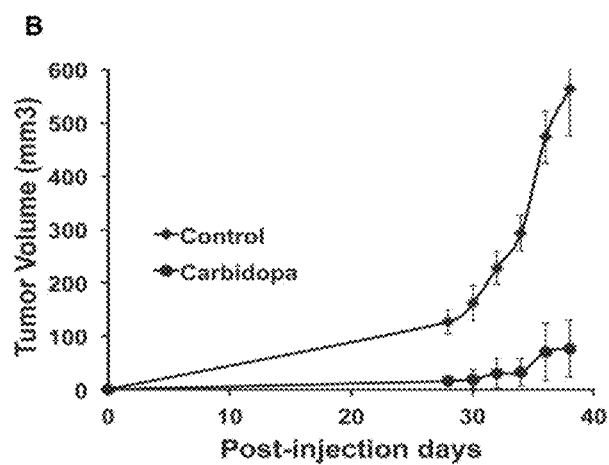

FIGS. 2A and 2B show the in vivo effect of Carbidopa on the growth of BxPC-3 cells in mouse xenografts. The cells were injected subcutaneously in athymic nude mice. Carbidopa (1 mg/mouse) was injected intraperitoneally (i.p.) two days prior to the injection of the tumor cells (prevention mode). Drug injection was continued every day at the same dose. Control mice did not receive Carbidopa. The growth of the tumor at the injected site was monitored every other day. Daily injection of Carbidopa reduced the growth of the tumor markedly.

Figure 3:
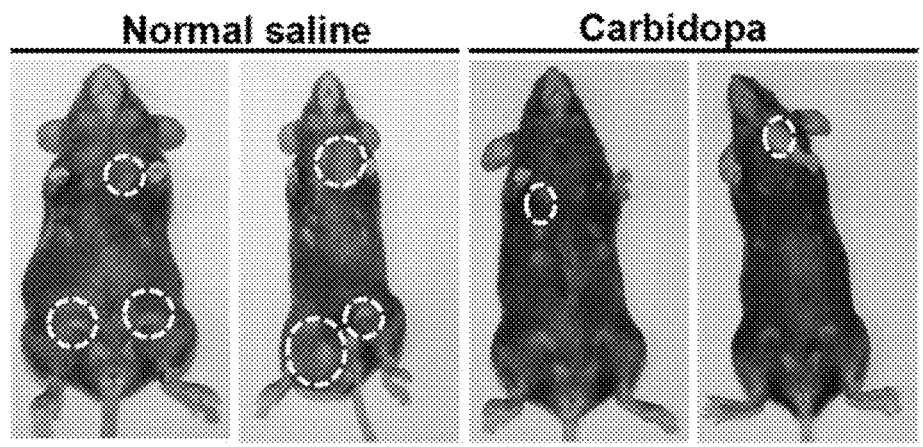
FIG. 3 shows the in vivo effect of Carbidopa on the growth of spontaneous breast cancer driven by the polyoma middle T antigen oncogene in mice (treatment for 2 months).

FIG. 3 shows the in vivo effect of Carbidopa on the growth of spontaneous breast cancer driven by the polyoma middle T antigen oncogene in mice (treatment for 2 months). The MMTV-PyMT-Tg mice develop spontaneous breast tumors within 2 months of age. We assessed the anticancer effect of Carbidopa in this mouse model by having two groups of mice, one control (no treatment; saline injection) and the other experimental (Carbidopa injection i.p. at 1 mg/mouse). The drug treatment was started at 4 weeks of age and continued for two months. The mice were photographed at the end of this experimental period. The circles indicate the tumor size in two representative control mice and two representative Carbidopa-treated mice. Carbidopa treatment reduced the number and size of the tumors in this mouse model of breast cancer.

Figure 4:
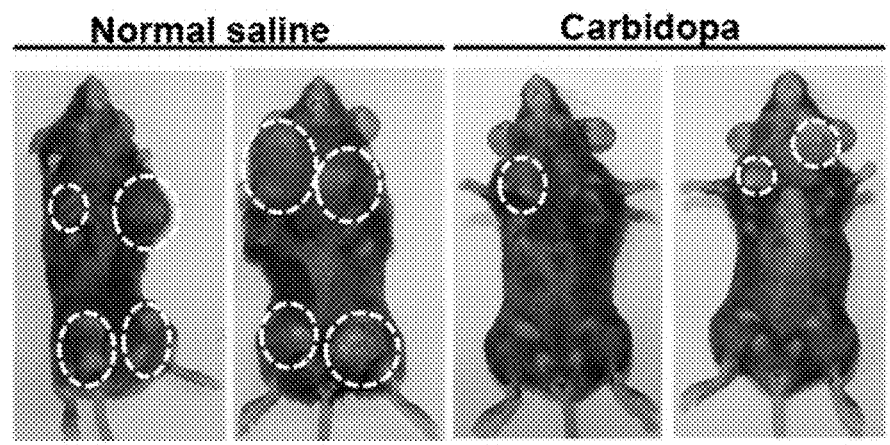
FIG. 4 shows the in vivo effect of Carbidopa on the growth of spontaneous breast cancer driven by the polyoma middle T antigen oncogene in mice (treatment for 3 months).

FIG. 4 shows the in vivo effect of Carbidopa on the growth of spontaneous breast cancer driven by the polyoma middle T antigen oncogene in mice (treatment for 3 months). The MMTV-PyMT-Tg mice develop spontaneous breast tumors within 2 months of age. The inventors assessed the anticancer effect of Carbidopa in this mouse model by having two groups of mice, one control (no treatment; saline injection) and the other experimental (Carbidopa injection intreaperitoneally (i.p.) at 1 mg/mouse). The drug treatment was started at 4 weeks of age and continued for three months. The mice were photographed at the end of the study period. The circles indicate the tumor size in two representative control mice and two representative Carbidopa-treated mice. Carbidopa treatment reduced the number and size of the tumors in this mouse model of breast cancer.

Figure 5:
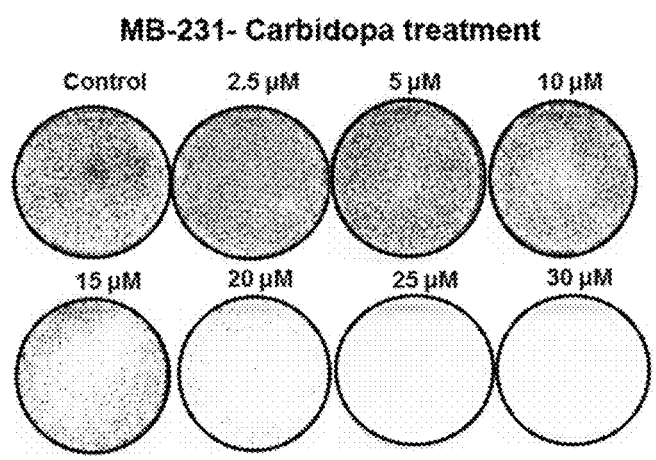
FIG. 5 shows the effect of Carbidopa on the growth of estrogen receptor-negative breast cancer cells in vitro.

FIG. 5 shows the effect of Carbidopa on the growth of estrogen receptor-negative breast cancer cells in vitro. Breast cancer occurs in different subtypes: estrogen receptor-positive, estrogen receptor-negative, and BRCA1-mutant. The MMTV-PyMT-Tg mice represent estrogen receptor-positive breast cancer at least at the initial stages. To assess the potential of Carbidopa for the treatment of ER-negative breast cancer, the inventors used the human breast cancer cell line MB-231, a well-established model to study ER-negative breast cancer in model systems. The inventors monitored the effect of Carbidopa (dose response) on the growth of these cells using the colony formation assay. Carbidopa showed marked inhibitory effect on the growth of these cells. 50% inhibition was observed at Carbidopa concentrations <15 µM. These data show that Carbidopa can be used not only for the treatment of ER-positive breast cancer (which represents ~75% of breast cancers in women) but also for the treatment of ER-negative breast cancer (which represents only ~10% breast cancers in women but is more aggressive than the ER-positive breast cancer and has not targeted therapy at this time).

FIG. 6 shows the effect of Carbidopa on the growth of BRCA-1 mutant breast cancer cells in vitro. Breast cancer occurs in different subtypes: estrogen receptor-positive, estrogen receptor-negative, and BRCA1-mutant. Mutations in BRCA-1 represent a small percentage of breast cancers in women but the disease is inheritable. There is increased public awareness on mutant BRCA-driven breast cancer because of the highly increased risk of breast cancer (also ovarian cancer) associated with the mutation and the availability of genetic screening for the disease-causing mutations. To assess the potential of Carbidopa for the treatment of mutant BRCA-1-driven breast cancer, the inventors used the human breast cancer cell line HCC-1937, a well-established model to study mutant BRCA-1-driven breast cancer in model systems. The inventors monitored the effect of Carbidopa (dose response) on the growth of these cells using the colony formation assay. Carbidopa showed marked inhibitory effect on the growth of these cells. 50% inhibition was observed at Carbidopa concentrations <25 µM. These data show that Carbidopa can also be used for the treatment of inheritable mutant BRCA-driven breast cancer.

FIG. 7 shows the effect of Carbidopa on the enzyme activity of recombinant human indoleamine dioxygenase-1 (IDO1). IDO-1 is an immunosuppressive enzyme that is induced in tumor cells and in immune cells present in tumor-draining lymph nodes. Induction of this enzyme suppresses the ability of the immune system to recognize tumor cells as foreign cells, which provides a means for the tumor cells to escape the immune attack. Pharmacological inhibition of this enzyme has potential in cancer treatment because such an approach will potentiate the ability of the immune system to kill the tumor cells. Many pharmaceutical companies have research programs in identifying selective inhibitors of IDO-1 for this purpose and some of the drugs are already in clinical trials in cancer patients. The present inventors assessed the ability of Carbidopa on the activity of this enzyme using the recombinant human enzyme. The inventors found that Carbidopa inhibits IDO-1 significantly at a concentration of 10 µM. This potency is comparable to that of the widely known IDO-1 inhibitor 1-methyltryptophan.

FIG. 8 is an immunohistochemical analysis of Ki-67, p-mTOR, HIF1α and Cyp1a1 protein expression in MMTV-PyMT-Tg mice treated with and without Carbidopa. Ki-67 staining shows a significant difference in cell proliferation with a marked reduction in proliferation in Carbidopa-treated mice. mTOR signaling is a master regulator of protein synthesis and constitutes a major antiapoptotic mechanism that confers survival advantage in cancer cells. Treatment of MMTV-PyMT-Tg mice with Carbidopa exhibits a marked reduction in p-mTOR staining, indicating that Carbidopa inhibits mTOR signaling. Hypoxia is a key regulatory factor in tumor progression and in response to the hypoxic tumor environment, it regulates cell metabolism and redox homeostasis. HIF1α level in tumors is controlled by mTOR. Carbidopa-treated mice show a marked decrease in HIF1α protein, confirming the suppression of mTOR signaling by Carbidopa. Indoleamine dioxygenase 1 (IDO1) is a tryptophan-catabolizing enzyme that is highly upregulated in various cancers. The inventors' data has hinted that the anti-proliferative effect of Carbidopa on cancer cells could be at least partly through inhibition of IDO1. To further validate the data, the inventors measured the expression of Cyp1a1 in MMTV-PyMT-Tg mice treated with and without Carbidopa. Cyp1a1 is an aryl hydrocarbon (AhR) receptor-responsive gene induced in response to AhR activation. AhR is activated by kynurenine, a product of IDO1 action on tryptophan. Thus, Cyp1a1 levels in tumor tissues serve as a read out for IDO1 activity. Carbidopa treatment showed a significant reduction in Cyp1a1 expression in tumor tissues, suggesting that Carbidopa is an inhibitor of IDO1. H&E, hematoxylin and eosin stain.

By way of explanation, and in no way a limitation of the present invention, Carbidopa elicits its anticancer effects at least via two mechanisms: inhibition of mTOR signaling and/or inhibition of IDO1. The inhibition of mTOR is an example of chemotherapy. Several mTOR inhibitors are in clinical use for cancer therapy. These studies demonstrate that Carbidopa also functions as an inhibitor of mTOR signaling pathway.

The inhibition of IDO1 is an example of immunotherapy. Inhibition of IDO1 in vivo may boost host immune system so that the immune cells can target the cancer cells for destruction. It is well known that tumor cells find a way to suppress the ability of the host immune system to evade destruction. Carbidopa reverses this effect. IDO1 inhibitors are in clinical trials for cancer treatment. There are other means to use the host immune system to fight against cancer. Carbidopa was used as an inhibitor of IDO1 functions as an anticancer drug at least partly via its ability to enhance the ability of immune cells to target tumor cells for destruction. Thus, the present inventors demonstrated for the first time that Carbidopa functions potentially both as a chemotherapeutic agent (mTOR inhibition) and as an immunotherapeutic agent (IDO1 inhibition). The novelty of Carbidopa for cancer treatment lies in its ability to serve as a single-agent to promote chemotherapy and immunotherapy.

The dose of Carbidopa used in mouse studies (1 mg/day/mouse) translated into <400 mg/day in patients weighing 60 kg (according to FDA conversion table). At this dose, Carbidopa has been shown to cause no unwanted side effects in humans; therefore, the drug has potential for use as an anticancer drug. In certain examples, the dosage may be 15 to 500, 25 to 450, 50 to 400, 70 to 100, 100 to 350, 150 to 300, 200 to 250, 15, 25, 50, 75, 100, 150, 200, 250, 300, 400, 450, 500 or 600 mg per day.

These studies demonstrate the efficacy of Carbidopa as a single agent. However, Carbidopa can also be used in combination with other conventional chemotherapy. For example, gemcitabine can be used in combination with Carbidopa to treat pancreatic cancer; taxol can be used in combination with Carbidopa to treat ER-positive breast cancer as well as treatment of Estrogen Receptor (ER)-negative or mutant BRCA-driven breast cancer.

Example 2

Most epidemiological studies have shown that Parkinson's disease (PD) patients have decreased incidence of most cancers, including pancreatic cancer, with the notable exceptions of melanoma and possibly breast cancer [1-5]. Most of these patients are treated with a combination-drug regimen consisting of Carbidopa and L-DOPA. Several studies have investigated the potential effect of L-DOPA on cancer, with an idea that the use of L-DOPA might be responsible for the decreased incidence of most cancers or for the increased incidence of melanoma in patients with PD [6-9]. But none of these studies showed evidence of involvement of L-DOPA in the decreased incidence of most cancers in association with PD, leaving the puzzling phenomenon unexplained. Interestingly, though Carbidopa is always used in combination with L-DOPA to treat PD, the potential relevance of Carbidopa to decreased cancer risk has never been investigated.

As dopaminergic neurons are selectively decreased in PD, L-DOPA is used to increase dopamine levels in the brain as the treatment strategy. Carbidopa on its own has no therapeutic effect in this disease, but is used in combination with L-DOPA to enhance the potency of the latter. Carbidopa is an analog of L-DOPA, having a methyl group and a hydrazine moiety attached to the α-carbon (FIG. 13). It is an inhibitor of aromatic amino acid decarboxylase, thus preventing the conversion of L-DOPA into dopamine (FIG. 13). However, the effect of Carbidopa is restricted to the peripheral tissues and the conversion of L-DOPA into dopamine in the brain is not affected by Carbidopa because of the inability of the latter to cross the blood-brain barrier [10, 11]. Dopamine also does not penetrate the blood-brain barrier; therefore the conversion of L-DOPA into dopamine outside the brain decreases the availability of the drug to the brain. As such, when used in combination with Carbidopa, more L-DOPA enters the brain for subsequent conversion into dopamine; thus, Carbidopa potentiates the therapeutic effect of L-DOPA in PD. At present, Carbidopa by itself is not indicated as a drug for any disease.

The present study was undertaken to test the hypothesis that Carbidopa, always used in combination with L-DOPA, is responsible for the decreased incidence of most cancers in patients with PD. For this hypothesis to be true, Carbidopa on its own must have anticancer effect. These studies presented here show that this indeed is the case; Carbidopa inhibits the growth and proliferation of pancreatic cancer cell lines in vitro and in vivo. Subsequent studies into the molecular mechanisms reveal that Carbidopa is an agonist for the nuclear receptor AhR (aryl hydrocarbon receptor), and that this function is observed at drug concentrations that are therapeutically relevant to patients with PD. These studies provide a plausible explanation as to why the cancer incidence is generally decreased in patients with PD. More importantly, these studies demonstrate that Carbidopa is an agonist for AhR and suppresses pancreatic cancer, suggesting that the drug could potentially be re-purposed to treat pancreatic cancer and possibly other cancers.

Cell culture. Human cell lines, hTERT-HPNE (normal pancreatic epithelial), BxPC-3, Capan-1, and Capan-2 (pancreatic cancer), and HepG2 (liver cancer) cells were all procured from ATCC. These cell lines were used within 10-20 passages. The ATCC has done morphological, cytogenetic and DNA profile analyses for characterization of these cell lines. AsPC-1, MIA PaCa-2, and Panc-1 human pancreatic cancer cell lines were obtained from Dr. Raj Govindarajan (Ohio State University, Columbus, Ohio, USA). HPDE, a human pancreatic ductal epithelial cell line, was kindly provided by Dr. Ming Tsao, Ontario Cancer Institute (Toronto, Canada). AsPC-1 and BxPC-3 cells were grown in RPMI-1640 medium, supplemented with 10% FBS and subcultured at a 1:5 ratio. hTERT-HPNE cells were maintained in 75% Dulbecco's Modified Eagle's Medium (DMEM) without glucose plus 25% Medium M3 Base with the following additives: 5% FBS, 5.5 mM D-glucose, 10 ng/mL human recombinant epidermal growth factor, and 750 ng/mL puromycin and subcultured at a 1:4 ratio. HPDE cells were cultured in Keratinocyte Serum Free Media supplemented with epidermal growth factor and bovine pituitary extract and subcultured at a 1:4 ratio. MIA PaCa-2 cells were cultured in DMEM, supplemented with 10% FBS and 2.5% horse serum, and subcultured at a 1:8 ratio. Capan-2 cells were cultured in McCoy's 5A Medium Modified supplemented with 10% FBS and subcultured at a 1:4 ratio. HepG2 cells were cultured in Eagle's Minimum Essential Media supplemented with 10% FBS and subcultured at a 1:4 ratio. All media for the above cell lines except HPDE (Fisher Scientific, Waltham, Mass., USA) and HPNE (Incell Corporation LLC, San Antonio, Tex., USA) were purchased from Mediatech (Manassas, Va., USA) and were supplemented with 100 units/mL penicillin and 2 μg/mL streptomycin. All these cell lines have been routinely tested for mycoplasma contamination using the Universal Mycoplasma Detection Kit obtained from ATCC. Mycoplasma-free cell lines were used in all these experiments.

RNA isolation, Reverse-Transcriptase PCR and real-time PCR. RNA was isolated from cells using Trizol. The expression of the various genes was analyzed using either Reverse transcriptase PCR or real-time PCR. After isolation, RNA concentration was measured using a Nanodrop ND-1000 system, followed by cDNA synthesis using high capacity cDNA synthesis kit (Invitrogen, Grand Island, N.Y., USA). Reverse transcriptase PCR was carried out under optimal conditions using a TaKaRa Taq Hot Start version (TaKaRa Bio USA Inc, Mountain View, Calif., USA). The following primer pairs were used: Human IDO1, forward 5'-CAG GCA GAT GTT TAG CAA TGA-3' (SEQ ID NO:1) and reverse 5'-GAT GAA GAA GTG GGC TTT GC-3' (SEQ ID NO:2); human AhR, forward 5'-TCA AAT CCT TCC AAG CGG CA-3' (SEQ ID NO:3) and reverse 5'-ACA GTT ATC CTG GCC TCC GT-3' (SEQ ID NO:4); human ARNT, forward 5'-CCG GCA GAG AAT TTC AGG AAT AG-3' (SEQ ID NO:5) and reverse 5'-GAA AGC TGC CCA CAC CAA AC-3' (SEQ ID NO:6); human HPRT, forward 5'-GCG TCG TGA TTA GCG ATG ATG AAC-3' (SEQ ID NO:7) and reverse 5'-CCT CCC ATC TCC TTC ATG ACA TCT-3' (SEQ ID NO:8). In real-time PCR the relative mRNA levels were measured with a SYBR Green detection system using StepOnePlus real-time PCR system (Applied Biosystems, Foster City, Calif., USA). The experiments were done in triplicates. The relative level of expression for each gene was calculated by normalizing the cycle threshold ($C_t$) value of the study gene to that of the housekeeping gene (hypoxanthine-guanine phosphoribosyltransferase-1 [HPRT1]). The following primer pairs were used: Human CYP1A1, forward 5'-CAA GGG GCG TTG TGT CTT TG-3' (SEQ ID NO:9) and reverse 5'-GTC GAT AGC ACC ATC AGG GG-3' (SEQ ID NO:10).

Immunofluorescence. Immunofluorescence studies were performed as described [12]. Briefly, cells grown on chamber slides were fixed, blocked and stained with mouse anti-AhR antibody (Abcam, Cambridge, Mass., USA) for 45 min after which they were washed and stained with secondary antibody (goat anti-mouse IgG) conjugated with Alexa Fluor 488 (Molecular Probes, Eugene, Oreg., USA); further washed and mounted with ProLong Diamond Antifade mountant with DAPI and the images were captured using a Nikon inverted microscope. Nuclei stained with DAPI are blue. Magnification, 100×.

Cell proliferation. Clonogenic assay was performed as described [12]. The cells were seeded at a very low density (500 cells/well) and allowed to attach to the substratum. They were then treated with 10 µM Carbidopa and the colonies were allowed to grow for two weeks. The wells were washed every other day and fresh Carbidopa was added to the wells. At the end of the two-week period, the wells were washed and the colonies were visualized with KaryoMax Giemsa stain after fixation with methanol. The stain was eluted with 1% sodium dodecyl sulfate in 0.2 NaOH and the absorbance was measured at 630 nm.

Computer modeling for the interaction of Carbidopa with IDO1. The potential interaction of Carbidopa with IDO1 was investigated using computer-based molecular docking modeling with AutoDock4 and Gold 5.0 programs. These programs predicted strong interaction of Carbidopa with the active site of IDO1 similar to phenylhydrazine, a known IDO1 inhibitor.

Xenograft studies. Female athymic nu/nu mice (8-week-old) were allowed to acclimatize to the environment for about a week before the start of the experiment. The animals were divided into control and treatment groups and injected with phosphate-buffered saline (control group) and Carbidopa @ 1 mg/mouse/day) (treatment group) intraperitoneally, at least 5 days prior to tumor cell injection. BxPC-3 ($10 \times 10^6$ cells in 30% matrigel) was injected subcutaneously at the right flank of the mice. The treatment continued all through the experimental period. Tumor size in different groups were measured using a caliper and the tumor volume was calculated using the formula (width$^2$×length)/2.

Inhibition of pancreatic cancer cell proliferation by Carbidopa and its potential relevance to the ability of the drug to inhibit IDO1. To test whether Carbidopa has anticancer effect, the inventors used pancreatic cancer as a model. For this, the inventors first conducted a colony formation assay with a human pancreatic normal cell line (hTERT-HPNE) and two human pancreatic cancer cell lines (BxPC-3 and Capan-2). Carbidopa (10 µM) significantly reduced the number of colonies in the cancer cell lines BxPC-3 and Capan-2 compared to untreated controls. This inhibitory effect was not seen in the normal pancreatic cell line hTERT-HPNE (FIG. 9A), suggesting that the inhibition of colony formation by Carbidopa was specific for cancer cells. To corroborate these in vitro data, the inventors performed subcutaneous xenografts in athymic nude mice using BxPC-3 cells. Carbidopa at a daily dose of 1 mg/mouse (intraperitoneal injection) significantly reduced the tumor volume compared to untreated controls (FIG. 9B). These data provided evidence that Carbidopa possesses the ability to inhibit the proliferation of cancer cells in vitro and growth of tumors in nude mice in vivo.

To date, the only known pharmacological action of Carbidopa is the inhibition of aromatic amino acid decarboxylase, but the inventors are not aware of any direct association between this enzyme and cancer. Therefore, the inventors looked for new, hitherto unknown, pharmacological actions for this drug that could be related to the observed anticancer effect. Carbidopa with its phenyl ring and a hydrazine moiety is structurally similar to phenylhydrazine, which is a potent inhibitor of indoleamine-2,3-dioxygenase 1 (IDO1) ($IC_{50}$; 8±2 µM); the inhibition occurs via interaction with heme at the active site of the enzyme [13]. IDO1 is a tryptophan-degrading enzyme [14] that is induced in antigen-presenting dendritic cells (DCs) in tumors and tumor-draining lymph nodes [15-18]. The increased activity of IDO1 in DCs depletes the essential amino acid tryptophan in the surroundings, suppresses proliferation of cytotoxic T cells and enables tumors to evade the immune system [19-22]. Tumor cells themselves also upregulate the expression of IDO1, suggesting potential involvement of the enzyme activity and also the resultant tryptophan metabolites as tumor promoters independent of the immune system [19]. Currently, IDO1 inhibitors are in clinical trials as anticancer drugs [23, 24]. The structural similarity between phenylhydrazine and Carbidopa suggested that the latter could also function as an IDO1 inhibitor. Though the anticancer effect of Carbidopa on pancreatic cancer cells was observed in this study in the absence of the immune system, it did not rule out the potential role of IDO1 inhibition by Carbidopa in tumor cells themselves. Therefore, the inventors first employed a computer-based molecular docking modeling using the programs AutoDock4 and Gold 5.0; phenylhydrazine was used as a positive control. The programs predicted the binding of phenylhydrazine with heme at the active site of the enzyme (FIG. 9C). A similar maneuver provided evidence for potential interaction of Carbidopa with the active site heme (FIG. 9D). This suggested that Carbidopa could function as an IDO1 inhibitor. To test the validity of the computer prediction, the inventors studied the effects of Carbidopa on human recombinant IDO1 by measuring the activity of the enzyme using a colorimetric assay. This experiment confirmed that Carbidopa does indeed inhibit IDO1 (FIG. 9E). During the assay the inventors discovered that the colorimetric assay was not suitable to determine accurately the efficacy of Carbidopa as an IDO1 inhibitor. The assay measures the product of the enzymatic activity, namely kynurenine, with the formation of a yellow-colored product, but Carbidopa itself gets oxidized while standing at room temperature to yield a yellow-colored product. As a result, the efficacy of Carbidopa for IDO1 inhibition deduced from the colorimetric assay was markedly underestimated. To assess the relevance of Carbidopa-induced inhibition of IDO1 to the anticancer effect of the drug, the inventors examined the expression of IDO1 in pancreatic cancer cell lines, primary tumors, and patient-derived xenografts (PDXs) in comparison with corresponding controls to ensure that IDO1 as the molecular target of Carbidopa was expressed in pancreatic cancer. The inventors found a significant increase in IDO1 expression in selective cancer cell lines (FIG. 9F) and in primary tumors (FIG. 9G). Surprisingly this was not the case in PDX samples (FIG. 14); there was either no change or a down-regulation in IDO1 expression in PDXs compared to normal pancreatic tissue samples. The inventors do not know the reasons for the discrepancy between primary tumors and PDXs; it could be due to the fact that the PDXs were generated by xenografting the primary tumors in nude mice 2-3 times. As these samples were grown in vivo in mice in the absence of an intact immune system, the expression of IDO1, an important immune-related enzyme, might have been altered in PDXs. Nonetheless, the data suggest that Carbidopa exhibits anticancer activity and that inhibition of IDO1 by the drug could possibly be related to this phenomenon.

Figure 15A:
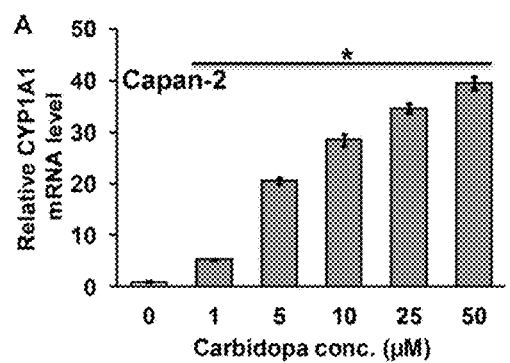
Figure 15B:
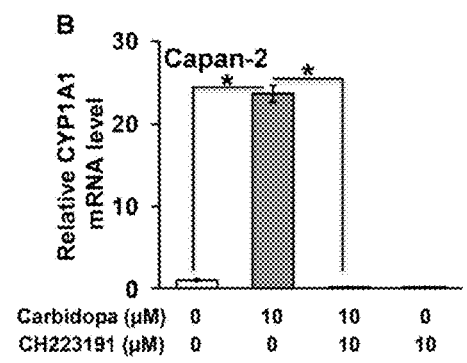
Figure 15C:
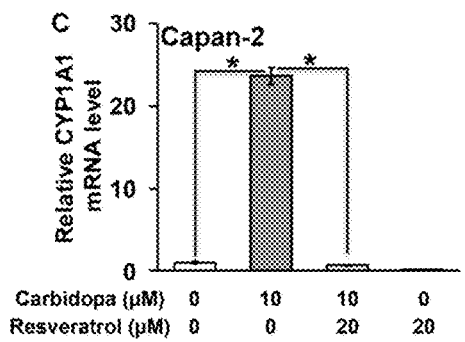
Figure 15D:
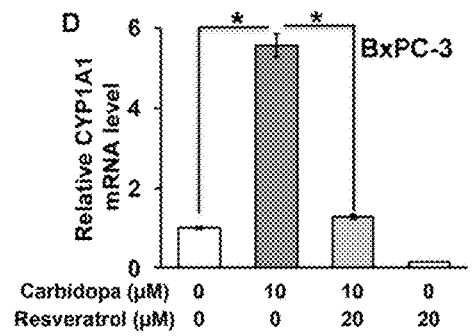

Carbidopa is a high-affinity agonist for the nuclear receptor AhR. The inventors realized the unsuitability of the colorimetric assay to accurately determine the potency of Carbidopa for the inhibition of IDO1, the inventors used an alternative approach. IDO1 degrades tryptophan and kynurenine is the product of this activity. Kynurenine is a known physiological agonist for the nuclear receptor AhR [25]. Agonist-induced activation of AhR is widely monitored by the induction of the AhR target gene CYP1A1 [26]. Therefore, the inventors decided to assess the efficacy of Carbidopa as an IDO1 inhibitor by monitoring CYP1A1 expression in intact cells. This rationale was simple (FIG. 10A). If Carbidopa inhibits IDO1 in an intact cell, kynurenine generation would be decreased, thus resulting in the suppression of AhR transcriptional activity, which can be monitored from decreased expression of CYP1A1 in Carbidopa-treated cells. Unliganded AhR resides in the cytoplasm, forming a complex with heat shock proteins. Upon binding an agonist, the cytoplasmic complex dissociates and the ligand-bound AhR gets translocated to the nucleus; AhR nuclear translocator (ARNT) facilitates the dissociation of the complex in the cytoplasm as well as the translocation of the ligand-bound AhR to the nucleus. The AhR-ARNT dimer then binds to a dioxin-responsive element (DRE) in target genes and induce transcription. CYP1A1 is one of the target genes [26]. Therefore, it should be possible to monitor the inhibition of IDO1 by Carbidopa by determining the efficacy of the drug on CYP1A1 expression; this approach would circumvent the drawback that the inventors encountered in the colorimetric assay. With this rationale, the inventors first checked the mRNA expression of AhR and its binding partner ARNT in BxPC-3 and Capan-2 cells (FIG. 10B). These genes were expressed in both pancreatic cancer cell lines. The inventors then treated these cancer cells with Carbidopa for 6 h and examined the expression levels of CYP1A1 mRNA. Surprisingly, these experiments produced results that were opposite to this original rationale. Carbidopa did not decrease CYP1A1 expression as expected; it increased the expression of this AhR target gene in a dose-dependent manner in BxPC-3 cells (FIG. 10C) as well as in Capan-2 cells (FIG. 15A). These data suggested that Carbidopa could actually be an agonist for AhR. To confirm that the Carbidopa-induced upregulation of CYP1A1 indeed occurred via AhR activation, the inventors used CH223191, an AhR-specific antagonist. The ability of Carbidopa to induce CYP1A1 was blocked by this antagonist in both BxPC-3 cells (FIG. 10D) and Capan-2 cells (FIG. 15B), clearly demonstrating the involvement of AhR activation in Carbidopa-induced expression of CYP1A1. To further corroborate this data, the inventors used resveratrol, another AhR antagonist; similar results were obtained in both cell lines (FIGS. 15C and 15D). Ligand-dependent activation of AhR is associated with the translocation of the receptor from the cytoplasm into nucleus. Therefore, the inventors used immunofluorescence to localize AhR in control and Carbidopa-treated BxPC-3 and Capan-2 cells. These studies provided evidence of nuclear translocation of the receptor in Carbidopa-treated cells (FIGS. 10E and 10F). These data provided strong evidence that Carbidopa is an agonist for AhR. This was a serendipitous discovery during the course of this efforts to characterize Carbidopa as an inhibitor of IDO1.

Liver is the major tissue where AhR activation plays a key role in xenobiotic metabolism. Therefore, the inventors decided to confirm these findings that Carbidopa is an AhR agonist using the human liver cell line HepG2. As expected, Carbidopa treatment led to CYP1A1 induction as early as 3 h post-treatment (FIG. 11A); the induction was dose-dependent (FIG. 11B). Under similar conditions, L-DOPA did not affect CYP1A1 expression. Furthermore, as observed in pancreatic cancer cells, AhR-specific antagonists CH223191 and resveratrol blocked Carbidopa-induced CYP1A1 expression (FIGS. 11C and 11D). Carbidopa treatment also led to the nuclear translocation of AhR (FIG. 11E).

With a fixed concentration (10 µM), the inventors compared in HepG2 cells the induction of CYP1A1 by Carbidopa with that by other known AhR agonists, which included 3-ethylcholanthrene, benzo[a]pyrene, kynurenine, indole-3-carbinol, and indole acetic acid (Table 1). Kynurenine is the only known physiological agonist for AhR, and the efficacy of Carbidopa to activate the receptor is in the same range as that of kynurenine.

TABLE 1

Effects of Carbidopa and known AhR agonists (10 micromolar) on CYP1A1 expression in HepG2 cells.

| Compound | Fold | [range] |
| --- | --- | --- |
| Carbidopa | 2.63 | [2.45-2.82] |
| 3-Methylcholanthrene | 56.8 | [54.7-59.0] |
| Benzo [a] pyrene | 35.3 | [32.4-38.5] |
| Kynurenine | 3.97 | [3.82-4.14] |
| Indole 3-carbinol | 7.62 | [7.37-7.88] |
| Indole acetic acid | 14.2 | [14.0-14.4] |

Upregulation of AhR in pancreatic cancer and its relationship to IDO1 expression. The studies described thus far have uncovered AhR as a novel pharmacologic target for Carbidopa; this drug is an agonist for AhR. To assess if this new molecular target for Carbidopa has any relevance to pancreatic cancer, the inventors examined the expression of AhR in pancreatic cancer cell lines, PDXs, and primary pancreatic tumor tissues. AhR expression was upregulated in the majority of the PDXs examined compared to normal pancreatic tissues (FIG. 12A). Pancreatic cancer cell lines also showed upregulation of AhR compared to normal cell lines (hTERT-HPNE and HPDE) (FIG. 12B). The same was also true with primary tumor samples (data not shown); this was in contrast to IDO1 expression where the expression patterns were different between PDXs and primary tumor tissues. The inventors also analyzed the publicly available microarray datasets for pancreatic cancer and found AhR upregulation in cancer (FIG. 12C), suggesting that AhR could serve as a drug target. The expression of IDO1 was also higher in tumor tissues compared to normal tissues (FIG. 12C). Interestingly, there was a direct correlation between AhR expression and IDO1 expression in tumor tissues. The biological relevance of this correlation remains unclear at this time. Though the data suggest that IDO1 could be a direct target for AhR, alternative explanations are also equally plausible. IDO1 activity produces kynurenine, the physiological agonist for AhR, and it is known that AhR activation induces AhR expression. Therefore, additional studies are needed to delineate the significance of the AhR-IDO1 correlation.

To summarize, these studies have uncovered two hitherto unknown molecular targets for Carbidopa, namely IDO1 and AhR. Carbidopa as an inhibitor of IDO1 was not a surprise based on the inhibition of IDO1 by phenylhydrazine, a structurally related compound. The finding that Carbidopa is an AhR agonist was a surprise. Many metabolites structurally related to tryptophan are AhR agonists [27], but all these metabolites possess an indole ring. In contrast, Carbidopa is a catechol. As such, Carbidopa as an AhR agonist is a novel finding. The dose-response data show that Carbidopa activates AhR at concentrations of 3-10 µM; these concentrations are therapeutically relevant. The recommended dose for Carbidopa in humans for the treatment of PD is 200 mg/day, but the drug is safe even at a dose as high as 450 mg/day [28]. With these doses of oral administration, plasma concentrations of the drug can reach levels sufficient to activate AhR (2 µM at 75 mg/day dose; 16 µM at 450 mg/day dose) [28]. The findings of the present study that Carbidopa at a dose of 1 mg/mouse/day is effective in blocking pancreatic tumor growth in vivo are also therapeutically relevant. This effective dose in mice translates to a human dose of <400 mg/day (Allometric scaling calculations from FDA Draft guidelines) [29, 30]. Currently the prevailing notion is that AhR and its ability to induce selective cytochrome p540 enzymes are primarily related to xenobiotic detoxification and to the efficacy of drugs, including anticancer drugs [31]. But recent studies have uncovered a critical role for AhR in cancer [32] and that AhR activation is effective to treat breast cancer, colon cancer and pancreatic cancer [33-36]. These findings that Carbidopa is an AhR agonist and an IDO1 inhibitor suggest that this drug has potential for cancer treatment. As Carbidopa is already used to treat PD, further investigations to potentially repurpose the drug for cancer treatment are clearly warranted.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention (s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Inzelberg, R. and Jankovic, J. (2007) Are Parkinson disease patients protected from some but not all cancers? Neurology 69, 1542-1550.
2. Bajaj, A., Driver, J. A. and Schernhammer, E. S. (2010) Parkinson's disease and cancer risk: a systematic review and meta-analysis. Cancer Causes Control 21, 597-707.
3. Sun, L. M., Liang, J. A., Chang, S. N., Sung, F. C., Muo, C. H., Kao, C. H. (2011) Analysis of Parkinson's disease and subsequent cancer risk in Taiwan: a nationwide population-based cohort study. Neuroepidemiology 37, 114-119.
4. Nikolaou, V. and Stratigos, A. J. (2014) Emerging trends in the epidemiology of melanoma. Br J Dermatol. 170, 11-19.
5. Disse, M., Reich, H., Lee, P. K. and Schram, S. S. (2016) A review of the association between Parkinson disease and malignant melanoma. Dermatol Surg. 42, 141-146.
6. Siple, J. F., Schneider, D. C., Wanlass, W. A. and Rosenblatt, B. K. (2000) Levodopa therapy and the risk of malignant melanoma. Ann Pharmacother. 34, 381-385.
7. Zanetti, R., Loria, D. and Rosso, S. (2006) Melanoma, Parkinson's disease and levodopa: causal or spurious link? A review of the literature. Melanoma Res. 16, 201-206.
8. Vermeij, J. D., Winogrodzka, A., Trip, J. and Weber, W. E. (2009) Parkinson's disease, levodopa-use and the risk of melanoma. Parkinsonism Relat Disord. 15, 551-553.
9. Inzelberg, R. and Israeli-Korn, S. D. (2009) The particular relationship between Parkinson's disease and malignancy: a focus on skin cancers. J Neural Transm. 116, 1503-1507.
10. Nagatsua, T. and Sawadab, M. (2009) L-Dopa therapy for Parkinson's disease: past, present, and future. Parkinsonism Relat Disord. 15 (Suppl 1), S3-S8.
11. LeWitt, P. A. (2015) Levodopa therapy for Parkinson's disease: Pharmacokinetics and pharmacodynamics. Mov Disord. 30, 64-72.
12. Coothankandaswamy, V., Cao, S., Xu, Y., Prasad, P. D., Singh, P. K., Reynolds, C. P., Yang, S., Ogura, J., Ganapathy, V. and Bhutia, Y. D. (2016) The amino acid transporter SLC6A14 is a novel and effective drug target for treatment of pancreatic cancer. Br J Pharmacol. 173, 3292-3306.
13. Fung, S. P., Wang, H., Tomek, P., Squire, C. J., Flanagan, J. U., Palmer, B. D., Bridewell, D. J., Tijono, S. M., Jamie, J. F. and Ching, L. M. (2013) Discovery and characterisation of hydrazines as inhibitors of the immune suppressive enzyme, indoleamine 2,3-dioxygenase 1 (IDO). Bioorg Med Chem. 21, 7595-7603.
14. Taylor, M. W. and Feng, G. S. (1991) Relationship between interferon-gamma, indoleamine 2,3-dioxygenase, and tryptophan catabolism. FASEB J. 5, 2516-2522.
15. Hwu, P., Du, M. X., Lapointe, R., Do, M., Taylor, M. W. and Young, H. A. Indoleamine 2,3-dioxygenase production by human dendritic cells results in the inhibition of T cell proliferation. J Immunol. 164, 3596-3599.
16. Munn, D. H., Sharma, M. D., Lee, J. R., Jhaver, K. G., Johnson, T. S., Keskin, D. B., Marshall, B., Chandler, P., Antonia, S. J. and Burgess, R. (2002) Potential regulatory function of human dendritic cells expressing indoleamine 2,3-dioxygenase. Science 297, 1867-1870.
17. Braun, D., Longman, R. S. and Albert, M. L. (2004) A two-step induction of indoleamine 2,3 dioxygenase (IDO) activity during dendritic-cell maturation. Blood 106, 2375-2381.
18. Munn, D. H., Sharma, M. D., Hou, D., Baban, B., Lee, J. R., Antonia, S. J., Messina, J. L., Chandler, P., Koni, P. A. and Mellor, A. L. (2004) Expression of indoleamine 2,3-dioxygenase by plasmacytoid dendritic cells in tumor-draining lymph nodes. J Clin Invest. 114, 280-290.
19. Muller, A. J. and Scherle, P. A. (2006) Targeting the mechanisms of tumoral immune tolerance with small-molecule inhibitors. Nat Rev Cancer 6, 613-625.
20. Munn, D. H. (2006) Indoleamine 2,3-dioxygenase, tumor-induced tolerance and counter-regulation. Curr Opin Immunol. 18, 220-225.
21. Munn, D. H. and Mellor, A. L. (2007) Indoleamine 2,3-dioxygenase and tumor-induced tolerance. J Clin Invest. 117, 1147-1154.
22. Mellor, A. L. and Munn, D. H. (2008) Creating immune privilege: active local suppression that benefits friends, but protects foes. Nat Rev Immunol. 8, 74-80.
23. 1-Methyl-D-tryptophan in treating patients with metastatic or refractory solid tumors that cannot be removed by surgery. https://clinicaltrials.gov/ct2/show/NCT00567931.

24. Vacchelli, E., Aranda, F., Eggermont, A., Sautes-Fridman, C., Tartour, E., Kennedy, E. P., Platten, M., Zitvogel, L., Kroemer, G. and Galluzzi, L. (2014) Trial watch: IDO inhibitors in cancer therapy. Oncoimmunology 3, e957994.
25. Opitz, C. A., Litzenburger, U. M., Sahm, F., Ott, M., Tritschler, I., Trump, S., Schumacher, T., Jestaedt, L., Schrenk, D., Weller, M. et al. (2011) An endogenous tumour-promoting ligand of the human aryl hydrocarbon receptor. Nature 478, 197-203.
26. Murray, I. A., Patterson, A. D. and Perdew, G. H. (2014) Aryl hydrocarbon receptor ligands in cancer: friend or foe. Nat Rev Cancer 14, 801-814.
27. Jin, U. H., Lee, S. O., Sridharan, G., Lee, K., Davidson, L. A., Jayaraman, A., Chapkin, R. S., Alaniz, R. and Safe, S. (2014) Microbiome-derived tryptophan metabolites and their aryl hydrocarbon receptor-dependent agonist and antagonist activities. Mol Pharmacol. 85, 777-88.
28. Brod, L. S., Aldred, J. L. and Nutt, J. G. (2012) Are high doses of carbidopa a concern? A randomized, clinical trial in Parkinson's disease. Mov Disord. 27, 750-753.
29. Reagan-Shaw, S., Nihal, M. and Ahmad, N. (2007) Dose translation from animal to human studies revisited. FASEB J. 22, 659-661.
30. Guidance for Industry. Estimating the maximum safe starting dose in initial clinical trials for therapeutics in adult healthy volunteers. Food and Drug Administration, Center for Drug Evaluation and Research (CDER). (www.fda.gov/downloads/Drugs/Guidances/UCM078932 pdf).
31. Androutsopoulos, V. P., Tsatsakis, A. M. and Spandidos, D. A. (2009) Cytochrome P450 CYP1A1: wider roles in cancer progression and prevention. BMC Cancer 9, 187.
32. Feng, S., Cao, Z. and Wang, X. (2013) Role of aryl hydrocarbon receptor in cancer. Biochim Biophys Acta 1836, 197-210.
33. Hall, J. M., Barhoover, M. A., Kazmin, D., McDonnell, D. P., Greenlee, W. F. and Thomas R. S. (2010) Activation of the aryl hydrocarbon receptor inhibits invasive and metastatic features of human breast cancer cells and promotes breast cancer cell differentiation. Mol Endocrinol. 24, 359-369.
34. Hanieh, H., Mohafez, O., Hairul-Islam, V I., Alzahrani, A., Ismail, M. B., Thirugnanasambantham, K. (2016) Novel aryl hydrocarbon receptor agonist suppresses migration and invasion of breast cancer cells. Plos One 11, e0167650.
35. Koliopanos, A., Kleef, J., Xiao, Y., Safe, S., Zimmerman, A., Büchler, M. W. and Friess, H. (2002) Increased arylhydrocarbon receptor expression offers a potential therapeutic target for pancreatic cancer. Oncogene 21, 6059-6070.
36. Diaz-Diaz, C. J., Ronnekleiv-Kelly, S. M., Nukaya, M., Geiger, P. G., Balbo, S., Dator, R., megna, B. W., Carney, P. R., Bradfield, C. A. and Kennedy. G. D. (2016) The aryl hydrocarbon receptor is a repressor of inflammation-associated colorectal tumorigenesis in mouse. Ann Surg. 264, 429-436.

What is claimed is:

1. A method of inhibiting or reducing mTOR signaling or inhibition of indoleamine dioxygenase-1 (IDO1) in a subject with a proliferative disease which comprises administering to the subject having or suspected to have the proliferative disease, a therapeutically or prophylactically effective amount of the compound of Formula I:

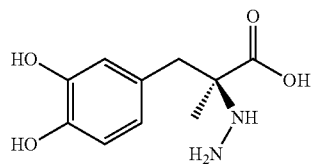 [SMILES: C[C@@](Cc1ccc(O)c(O)c1)(NN)C(=O)O]

or a pharmaceutically acceptable salt or solvate thereof in an amount sufficient to inhibit or reduce mTOR signaling or inhibit indoleamine dioxygenase-1 (IDO1) activity, wherein the proliferative disease is selected from at least one of a leukemia, myeloma, myeloproliferative disease, myelodysplastic syndrome, idiopathic hypereosinophilic syndrome (HES), bladder cancer, breast cancer, Estrogen Receptor (ER)-negative or mutant BRCA-driven breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, renal cancer, salivary gland cancer, small cell lung cancer, skin cancer, stomach cancer, testicular cancer, thyroid cancer, uterine cancer, and hematologic malignancy.

2. The method of claim 1, wherein the therapeutically or prophylactically effective amounts are from about 15 to 500, 25 to 450, 50 to 400, 70 to 100, 100 to 350, 150 to 300, 200 to 250, 15, 25, 50, 75, 100, 150, 200, 250, 300, 400, 450, 500 or 600 mg per day.

3. The method of claim 1, wherein the compound is administered at least one of continuously, intermittently, systemically, or locally.

4. The method of claim 1, wherein IDO1 is defined further as a human IDO1.

5. The method of claim 1, wherein the compound is administered orally, intravenously, or intraperitoneally.

6. The method of claim 1, wherein the Carbidopa is at least one of Carbidopa Besylate, Carbidopa Phosphate, Carbidopa Lactate, Carbidopa Hydrochloride, Carbidopa Citrate, Carbidopa Acetate, Carbidopa Toluenesulphonate, Carbidopa Succinate, or Carbidopa Besylate.

7. The method of claim 1, wherein the mTOR is a human mTOR.

8. The method of claim 1, wherein the therapeutically or prophylactically effective amount of compound is administered daily for as long as the subject is in need of treatment for the proliferative disease.

9. The method of claim 1, wherein the compound is provided at least one of sequentially or concomitantly, with another pharmaceutical agent in a newly diagnosed proliferative disease subject, to maintain remission of an existing subject, or a relapsed/refractory proliferative disease subject.

10. The method of claim 1, wherein the compound is provided as a single agent or in combination with another pharmaceutical agent in a newly diagnosed proliferative disease subject, to maintain remission, or a relapsed/refractory proliferative disease subject.

11. The method of claim 1, wherein the compound is provided as a single agent or in combination with another pharmaceutical agent in a newly diagnosed proliferative disease pediatric subject, to maintain remission, or a relapsed/refractory proliferative disease pediatric.

12. The method of claim 1, wherein the compound is provided in an amount sufficient to inhibit or reduce mTOR signaling or inhibit IDO1.

13. A method for treating a subject with a proliferative disease comprising:
administering to the subject in need of such treatment a therapeutically effective amount of Carbidopa or a salt thereof, wherein the cell proliferative disorder is characterized by the need to inhibit or reduce mTOR signaling or inhibit IDO1, wherein the therapeutically effective amount is sufficient to in an amount sufficient to inhibit or reduce mTOR signaling or inhibit indoleamine dioxygenase-1 (IDO1) activity, wherein the proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, renal cancer, salivary gland cancer, small cell lung cancer, skin cancer, stomach cancer, testicular cancer, thyroid cancer, uterine cancer, or hematologic malignancy.

14. The method of claim 13, wherein the compound is administered orally, intravenously, or intraperitoneally.

15. The method of claim 13, wherein the Carbidopa is at least one of Carbidopa Besylate, Carbidopa Phosphate, Carbidopa Lactate, Carbidopa Hydrochloride, Carbidopa Citrate, Carbidopa Acetate, Carbidopa Toluenesulphonate, Carbidopa Succinate or Carbidopa Besylate.

16. The method of claim 13, wherein the Carbidopa is provided at least one of sequentially or concomitantly, with chemotherapy, radiotherapy, or surgery in a newly diagnosed proliferative disease, to maintain remission, or a relapsed/refractory proliferative disease.

17. The method of claim 13, wherein the Carbidopa is provided as a single agent or in combination with chemotherapy, radiotherapy or surgery for treatment of pediatric subject with the proliferative disease.

18. The method of claim 13, wherein the Carbidopa is provided as a single agent to at least one of post standard induction therapy, or high dose induction therapy, in newly diagnosed proliferative disease.

19. The method of claim 13, wherein the Carbidopa is provided as a single agent in treatment of subjects with the proliferative disease that is either refractory to, or has relapsed after, standard or high dose chemotherapy, radiotherapy or surgery.

20. The method of claim 13, wherein the subject is refractory to a prior anti-neoplastic therapy.

21. The method of claim 13, wherein the method further comprises the step of identifying a subject in need of treatment for a proliferative disease prior to treatment.

22. A method for treating a subject with breast or pancreatic cancer comprising:
obtaining a sample from the subject suspected of having breast or pancreatic cancer;
determining from the subject sample that the subject has a need of inhibiting or reducing mTOR signaling or inhibition of indoleamine dioxygenase-1 (IDO1); and administering to the subject in need of such treatment a therapeutically effective amount of Carbidopa or a salt thereof, wherein the breast or pancreatic cancer is characterized by the need to inhibit or reduce mTOR signaling or inhibit IDO1.

23. A method for specifically inhibiting or reducing mTOR signaling or inhibition of indoleamine dioxygenase-1 (IDO1) in a subject comprising:
determining if the subject has a proliferative disease;
obtaining a subject sample to determine a need to inhibit or reduce mTOR signaling or inhibit IDO1; and
administering to a mammal in need of such treatment a therapeutically effective amount of Carbidopa or a salt thereof sufficient inhibit or reduce mTOR signaling or inhibit IDO1 in the mammal, wherein the proliferative disease is selected from at least one of a leukemia, myeloma, myeloproliferative disease, myelodysplastic syndrome, idiopathic hypereosinophilic syndrome (HES), bladder cancer, breast cancer, Estrogen Receptor (ER)-negative or mutant BRCA-driven breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, renal cancer, salivary gland cancer, small cell lung cancer, skin cancer, stomach cancer, testicular cancer, thyroid cancer, uterine cancer, and hematologic malignancy.

24. The method of claim 22, wherein the therapeutically and prophylactically effective amounts of Carbidopa or a salt thereof are from about 15 to 500 mg per day.

25. The method of claim 22, wherein the Carbidopa or a salt thereof is administered at least one of continuously, intermittently, systemically, or locally.

26. The method of claim 22, wherein the mTOR is a human mTOR.

27. The method of claim 22, wherein the compound is administered orally, intravenously, or intraperitoneally.

28. The method of claim 22, wherein the Carbidopa is at least one of Carbidopa Besylate, Carbidopa Phosphate, Carbidopa Lactate, Carbidopa Hydrochloride, Carbidopa Citrate, Carbidopa Acetate, Carbidopa Toluenesulphonate and Carbidopa Succinate Carbidopa Besylate.

29. The method of claim 22, wherein the IDO1 is a human IDO1.

30. The method of claim 22, wherein the therapeutically or prophylactically effective amount of the compound is administered daily for as long as the subject is in need of treatment for the proliferative disease.

31. The method of claim 22, wherein the subject is provided treatment, and the method further comprises the steps of: obtaining one or more subject samples to determine the effect of the treatment, and continuing treatment until the proliferative disease is reduced or eliminated.

32. The method of claim 22, wherein the compound is provided at least one of sequentially or concomitantly, with another pharmaceutical agent in a newly diagnosed proliferative disease subject, to maintain remission, or a relapsed/refractory proliferative disease subject.

33. The method of claim 22, wherein the compound is provided as a single agent or in combination with another pharmaceutical agent in a newly diagnosed proliferative disease subject, to maintain remission, or a relapsed/refractory proliferative disease subject.

34. The method of claim 22, wherein the compound is provided as a single agent or in combination with another pharmaceutical agent in a newly diagnosed proliferative disease pediatric subject, to maintain remission, or a relapsed/refractory proliferative disease pediatric subject.

* * * * *